US008273043B2

(12) United States Patent
Bonutti et al.

(10) Patent No.: US 8,273,043 B2
(45) Date of Patent: Sep. 25, 2012

(54) ORTHOSIS APPARATUS AND METHOD OF USING AN ORTHOSIS APPARATUS

(75) Inventors: Peter M. Bonutti, Effingham, IL (US);
Boris P. Bonutti, Effingham, IL (US);
Kevin R. Ruholl, Effingham, IL (US);
Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 1036 days.

(21) Appl. No.: 12/180,400

(22) Filed: Jul. 25, 2008

(65) Prior Publication Data

US 2009/0030353 A1   Jan. 29, 2009

Related U.S. Application Data

(60) Provisional application No. 60/951,726, filed on Jul. 25, 2007, provisional application No. 61/033,786, filed on Mar. 4, 2008.

(51) Int. Cl.
*A61F 5/00* (2006.01)
(52) U.S. Cl. .............................. 602/23; 602/26; 602/27
(58) Field of Classification Search .................... 602/13, 602/20–22, 26–27, 23; 128/878–879, 882; 601/5, 33
See application file for complete search history.

(56) References Cited

U.S. PATENT DOCUMENTS

| | | | |
|---|---|---|---|
| 432,327 A | 7/1890 | Page | |
| 433,227 A | 7/1890 | Beacock | |
| 2,191,283 A | 2/1940 | Longfellow | |
| 2,206,902 A | 7/1940 | Kost | |
| 2,223,276 A | 11/1940 | Ward | |
| 2,237,252 A | 4/1941 | Longfellow | |
| 2,246,689 A | 6/1941 | Kost | |
| 2,250,493 A | 7/1941 | Milne | |
| 2,590,729 A | 3/1952 | Scognamillo | |
| 2,590,739 A | 3/1952 | Wanner et al. | |
| 2,811,154 A | 10/1957 | Scholl | |
| 2,820,455 A | 1/1958 | Hall | |

(Continued)

FOREIGN PATENT DOCUMENTS

CA       2066151       10/1992

(Continued)

OTHER PUBLICATIONS

Joint Active Sytems, Inc., JAS; The Proven Approach to Restoring ROM (online), Copyright 2004 www.jointactivesystems.com.

(Continued)

*Primary Examiner* — Michael A. Brown
(74) *Attorney, Agent, or Firm* — Armstrong Teasdale LLP

(57) ABSTRACT

The present invention provides a new and improved orthosis for use in effecting relative movement between bones in an arm of a patient. The apparatus includes a lower cuff gripping distal bone, such as a wrist, and an upper cuff gripping a proximal bone, such as an upper arm. The lower cuff is secured in a rotatable drive assembly substantially coincident to a longitudinal axis of a medial bone, such as the forearm, during rotational distal adjustment. The angle between the forearm and the upper arm is adjustable and can be securely fixed at a desired angle. The rotation of the rotatable drive assembly effectuates the pronation and supination of the hand and wrist relative to the patient's forearm. The orthosis of the present invention can be disassembled with interchanging parts substituted depending on the patient's needs.

48 Claims, 23 Drawing Sheets

U.S. PATENT DOCUMENTS

| | | | |
|---|---|---|---|
| 2,829,562 A | 4/1958 | La Rue | |
| 2,832,334 A | 4/1958 | Whitelaw | |
| 3,083,708 A | 4/1963 | Gottfried | |
| 3,338,237 A | 8/1967 | Sconce | |
| 3,351,055 A | 11/1967 | Gottfried | |
| 3,548,818 A | 12/1970 | Kaplan | |
| 3,580,248 A | 5/1971 | Larson | |
| 3,698,389 A | 10/1972 | Guedel | |
| 3,701,349 A | 10/1972 | Larson | |
| 3,724,452 A | 4/1973 | Nitschke | |
| 3,760,056 A | 9/1973 | Rudy | |
| 3,795,243 A | 3/1974 | Miller | |
| 3,811,434 A | 5/1974 | Jacobson et al. | |
| 3,814,419 A | 6/1974 | Bjorklund et al. | |
| 3,856,004 A | 12/1974 | Cox | |
| 3,955,565 A | 5/1976 | Johnson, Jr. | |
| 3,970,316 A | 7/1976 | Westmoreland, Jr. | |
| 3,976,057 A | 8/1976 | Barclay | |
| 4,039,183 A | 8/1977 | Sakurada | |
| 4,076,022 A | 2/1978 | Walker | |
| 4,084,267 A | 4/1978 | Zadina | |
| 4,108,170 A | 8/1978 | Spann | |
| 4,180,870 A * | 1/1980 | Radulovic et al. | 623/26 |
| 4,214,577 A | 7/1980 | Hoy | |
| 4,229,001 A | 10/1980 | Roman | |
| 4,237,873 A | 12/1980 | Terry et al. | |
| 4,241,731 A | 12/1980 | Pauley | |
| 4,273,113 A | 6/1981 | Hofstein | |
| 4,285,773 A | 8/1981 | Taciuk | |
| 4,320,748 A | 3/1982 | Racette et al. | |
| 4,363,481 A | 12/1982 | Erickson | |
| 4,370,977 A | 2/1983 | Mauldin et al. | |
| 4,383,523 A | 5/1983 | Schurman | |
| 4,417,569 A | 11/1983 | Brudny | |
| 4,441,489 A | 4/1984 | Evans et al. | |
| 4,454,871 A | 6/1984 | Mann et al. | |
| 4,456,001 A | 6/1984 | Pescatore | |
| 4,456,002 A | 6/1984 | Barber et al. | |
| 4,502,470 A | 3/1985 | Kiser et al. | |
| 4,502,681 A | 3/1985 | Blomqvist | |
| 4,508,111 A | 4/1985 | Hepburn | |
| 4,509,509 A | 4/1985 | Bouvet et al. | |
| 4,538,595 A | 9/1985 | Hajianpour | |
| 4,538,600 A | 9/1985 | Hepburn | |
| 4,570,619 A | 2/1986 | Gamm | |
| 4,576,151 A | 3/1986 | Carmichael et al. | |
| 4,589,406 A | 5/1986 | Florek | |
| 4,606,542 A | 8/1986 | Segal | |
| 4,612,919 A | 9/1986 | Best | |
| 4,628,913 A | 12/1986 | Lerman | |
| 4,641,639 A | 2/1987 | Padilla | |
| 4,653,479 A | 3/1987 | Maurer | |
| 4,665,905 A | 5/1987 | Brown | |
| 4,693,239 A | 9/1987 | Clover, Jr. | |
| 4,716,889 A | 1/1988 | Saringer | |
| 4,718,665 A | 1/1988 | Airy et al. | |
| 4,727,865 A | 3/1988 | Hill-Byrne | |
| 4,739,334 A | 4/1988 | Soref | |
| 4,765,320 A | 8/1988 | Lindemann et al. | |
| 4,788,941 A | 12/1988 | Villeneuve | |
| 4,790,301 A | 12/1988 | Silfverskiold | |
| 4,793,334 A | 12/1988 | McGuinness et al. | |
| 4,805,601 A | 2/1989 | Eischen, Sr. | |
| 4,807,601 A | 2/1989 | Wright | |
| 4,809,688 A | 3/1989 | Aymerica del Valle et al. | |
| 4,834,073 A | 5/1989 | Bledsoe et al. | |
| 4,844,094 A | 7/1989 | Grim | |
| 4,844,454 A | 7/1989 | Rogers | |
| 4,844,455 A | 7/1989 | Funkhouser, Jr. | |
| 4,848,326 A | 7/1989 | Lonardo | |
| 4,862,877 A | 9/1989 | Barber | |
| 4,865,024 A | 9/1989 | Hensley et al. | |
| 4,869,267 A | 9/1989 | Grim et al. | |
| 4,869,499 A | 9/1989 | Schiraldo | |
| 4,884,454 A | 12/1989 | Johnson | |
| 4,913,135 A | 4/1990 | Mattingly | |
| 4,913,755 A | 4/1990 | Grim | |
| 4,930,497 A | 6/1990 | Saringer | |
| 4,953,543 A | 9/1990 | Grim et al. | |
| 4,955,369 A | 9/1990 | Bledsoe et al. | |
| 4,955,396 A | 9/1990 | Fralick et al. | |
| 4,957,281 A | 9/1990 | Christolear, Jr. | |
| 4,964,402 A | 10/1990 | Grim et al. | |
| 4,991,234 A | 2/1991 | Greenberg | |
| 4,996,979 A | 3/1991 | Grim et al. | |
| 5,005,563 A | 4/1991 | Veale | |
| 5,018,514 A | 5/1991 | Grood et al. | |
| 5,019,050 A | 5/1991 | Lynn et al. | |
| 5,025,782 A | 6/1991 | Salerno | |
| 5,027,688 A | 7/1991 | Suzuki et al. | |
| 5,027,801 A | 7/1991 | Grim | |
| 5,027,802 A | 7/1991 | Donohue | |
| 5,036,837 A | 8/1991 | Mitchell et al. | |
| 5,036,838 A | 8/1991 | Sherman | |
| 5,052,375 A | 10/1991 | Stark et al. | |
| 5,070,866 A | 12/1991 | Alexander et al. | |
| 5,078,128 A | 1/1992 | Grim et al. | |
| 5,088,481 A | 2/1992 | Darby | |
| 5,100,403 A | 3/1992 | Hotchkiss et al. | |
| 5,102,411 A | 4/1992 | Hotchkiss et al. | |
| 5,116,359 A | 5/1992 | Moore | |
| 5,125,400 A | 6/1992 | Johnson, Jr. | |
| 5,135,470 A | 8/1992 | Reeves | |
| 5,139,475 A | 8/1992 | Robicsek | |
| 5,141,489 A | 8/1992 | Sereboff | |
| 5,156,589 A | 10/1992 | Langen et al. | |
| 5,163,451 A | 11/1992 | Grellas | |
| 5,167,612 A | 12/1992 | Bonutti | |
| 5,191,903 A | 3/1993 | Donohue | |
| 5,197,942 A | 3/1993 | Brady | |
| 5,201,702 A | 4/1993 | Mars | |
| 5,201,772 A | 4/1993 | Maxwell | |
| 5,203,321 A | 4/1993 | Donovan et al. | |
| 5,211,161 A | 5/1993 | Stef | |
| 5,213,094 A | 5/1993 | Bonutti | |
| 5,213,095 A | 5/1993 | Dague | |
| 5,218,954 A | 6/1993 | van Bemmelen | |
| 5,226,245 A | 7/1993 | Lamont | |
| 5,232,435 A | 8/1993 | Leibinsohn | |
| 5,252,101 A | 10/1993 | Rosenwinkel et al. | |
| 5,252,102 A | 10/1993 | Singer et al. | |
| 5,261,125 A | 11/1993 | Cartwright et al. | |
| 5,277,695 A | 1/1994 | Johnson, Jr. et al. | |
| 5,285,773 A | 2/1994 | Bonutti et al. | |
| 5,297,540 A | 3/1994 | Kaiser et al. | |
| 5,312,322 A | 5/1994 | Santana | |
| 5,316,022 A | 5/1994 | Schiek, Sr. | |
| 5,323,435 A | 6/1994 | Baversten | |
| RE34,661 E | 7/1994 | Grim | |
| 5,327,882 A | 7/1994 | Saringer et al. | |
| 5,328,448 A | 7/1994 | Gray, Sr. | |
| 5,329,705 A | 7/1994 | Grim et al. | |
| 5,348,530 A | 9/1994 | Grim et al. | |
| 5,349,956 A | 9/1994 | Bonutti | |
| 5,352,216 A | 10/1994 | Shiono et al. | |
| 5,354,260 A | 10/1994 | Cook | |
| 5,364,323 A | 11/1994 | Liu | |
| 5,365,947 A | 11/1994 | Bonutti | |
| 5,370,133 A | 12/1994 | Darby et al. | |
| 5,372,597 A | 12/1994 | Hotchkiss et al. | |
| 5,376,091 A | 12/1994 | Hotchkiss et al. | |
| 5,378,223 A | 1/1995 | Grim et al. | |
| 5,385,536 A | 1/1995 | Burkhead et al. | |
| 5,389,065 A | 2/1995 | Johnson, Jr. | |
| 5,391,132 A | 2/1995 | Greenwald | |
| 5,395,303 A | 3/1995 | Bonutti et al. | |
| 5,399,152 A | 3/1995 | Habermeyer et al. | |
| 5,403,265 A | 4/1995 | Berguer et al. | |
| 5,407,420 A | 4/1995 | Bastyr et al. | |
| 5,407,422 A | 4/1995 | Matthijs et al. | |
| 5,417,643 A | 5/1995 | Taylor | |
| 5,419,757 A | 5/1995 | Daneshvar | |
| 5,421,874 A | 6/1995 | Pearce | |
| 5,435,009 A | 7/1995 | Schild et al. | |
| 5,437,611 A | 8/1995 | Stern | |
| 5,452,205 A | 9/1995 | Telepko | |
| 5,453,075 A | 9/1995 | Bonutti et al. | |

| | | | | | | |
|---|---|---|---|---|---|---|
| 5,453,082 | A | 9/1995 | Lamont | 6,572,571 B2 | 6/2003 | Lowe |
| 5,456,268 | A | 10/1995 | Bonutti | 6,575,926 B2 | 6/2003 | Bonutti |
| 5,456,286 | A | 10/1995 | Warner et al. | 6,599,255 B2 | 7/2003 | Zhang |
| 5,464,385 | A | 11/1995 | Grim | 6,599,263 B1 * | 7/2003 | Bonutti et al. ............ 602/20 |
| 5,466,213 | A | 11/1995 | Hogan et al. | 6,637,429 B2 | 10/2003 | Mundrick et al. |
| 5,466,250 | A | 11/1995 | Johnson, Jr. et al. | 6,682,497 B2 | 1/2004 | Jensen et al. |
| 5,472,407 | A | 12/1995 | Schenck | 6,743,187 B2 | 6/2004 | Solomon |
| 5,492,133 | A | 2/1996 | McVicker | 6,770,047 B2 | 8/2004 | Bonutti |
| 5,503,619 | A | 4/1996 | Bonutti | 6,890,285 B2 | 5/2005 | Rahman et al. |
| 5,503,622 | A | 4/1996 | Wehr | 6,921,377 B2 | 7/2005 | Bonutti |
| 5,503,908 | A | 4/1996 | Faass | 6,929,616 B2 * | 8/2005 | Bonutti et al. ............ 602/20 |
| 5,518,009 | A | 5/1996 | Ruiz-Gonzalez | 6,958,048 B2 | 10/2005 | Bonutti |
| 5,520,181 | A | 5/1996 | Kreidler et al. | 6,974,431 B2 | 12/2005 | Jensen |
| 5,520,628 | A | 5/1996 | Wehr | 7,101,347 B2 | 9/2006 | Culhane et al. |
| 5,527,269 | A | 6/1996 | Reithofer | 7,112,179 B2 | 9/2006 | Bonutti et al. |
| 5,531,669 | A | 7/1996 | Varnau | 7,182,738 B2 | 2/2007 | Bonutti et al. |
| 5,535,274 | A | 7/1996 | Braitberg et al. | 7,204,814 B2 | 4/2007 | Peles |
| 5,538,486 | A | 7/1996 | France et al. | 7,306,573 B2 | 12/2007 | Bonutti |
| 5,571,077 | A | 11/1996 | Klearman et al. | 7,404,804 B2 | 7/2008 | Bonutti |
| 5,577,998 | A | 11/1996 | Johnson, Jr. et al. | 2001/0047209 A1 | 11/2001 | Solomon |
| 5,605,535 | A | 2/1997 | Lepage | 2002/0029784 A1 | 3/2002 | Stark |
| 5,609,570 | A | 3/1997 | Lamont | 2002/0183655 A1 | 12/2002 | Zhang |
| 5,611,764 | A | 3/1997 | Bonutti et al. | 2004/0153010 A1 | 8/2004 | Bonutti |
| 5,620,411 | A | 4/1997 | Schumann et al. | 2004/0215120 A1 | 10/2004 | Jensen |
| 5,626,537 | A | 5/1997 | Danyo et al. | 2006/0036205 A1 | 2/2006 | Bonutti |
| 5,647,378 | A | 7/1997 | Farnum | 2007/0038161 A1 | 2/2007 | Bonutti et al. |
| 5,653,680 | A | 8/1997 | Cruz | 2007/0055190 A1 | 3/2007 | Bonutti et al. |
| 5,665,059 | A | 9/1997 | Klearman et al. | 2007/0100267 A1 | 5/2007 | Bonutti et al. |
| 5,681,269 | A | 10/1997 | Basaj et al. | 2007/0135738 A1 | 6/2007 | Bonutti et al. |
| 5,685,830 | A | 11/1997 | Bonutti | 2007/0197605 A1 | 8/2007 | Glombik et al. |
| 5,755,679 | A | 5/1998 | Selner et al. | 2007/0219475 A1 | 9/2007 | Bonutti et al. |
| 5,761,834 | A | 6/1998 | Grim et al. | 2007/0219476 A1 | 9/2007 | Bonutti et al. |
| 5,772,619 | A | 6/1998 | Corbett | 2008/0091132 A1 | 4/2008 | Bonutti |
| 5,778,565 | A | 7/1998 | Holt et al. | 2008/0188356 A1 | 8/2008 | Bonutti |
| 5,788,659 | A | 8/1998 | Haas | | | |
| 5,792,084 | A | 8/1998 | Wilson et al. | | | |

FOREIGN PATENT DOCUMENTS

| | | |
|---|---|---|
| CA | 2065669 | 10/1993 |
| DE | 2829562 | 1/1980 |
| DE | 8806231.7 | 5/1988 |
| DE | 8806231.7 | 6/1988 |
| DE | 405327 | 10/2024 |
| EU | 0181668 | 5/1986 |
| EU | 0181688 | 5/1986 |
| EU | 0380060 | 1/1990 |
| EU | 0510840 | 10/1992 |
| FR | 2661333 | 4/1990 |
| JP | 4261657 | 9/1992 |
| JP | 2001 087296 | 4/2001 |
| SU | 1158195 | 5/1985 |
| SU | 1426580 | 9/1988 |
| SU | 1671296 | 8/1991 |
| WO | WO 88/04543 | 6/1988 |
| WO | WO 2004/073143 | 1/2004 |
| WO | WO 2005/086741 | 9/2005 |
| WO | WO 2007/051168 | 5/2007 |
| WO | WO 2007/109638 | 9/2007 |
| WO | WO 2008/036895 | 8/2008 |

| | | | |
|---|---|---|---|
| 5,820,577 | A | 10/1998 | Taylor |
| 5,823,975 | A | 10/1998 | Stark et al. |
| 5,833,639 | A | 11/1998 | Nunes et al. |
| 5,839,139 | A | 11/1998 | Fink |
| 5,848,979 | A * | 12/1998 | Bonutti et al. ............ 601/5 |
| 5,865,773 | A | 2/1999 | Koledin |
| 5,882,320 | A | 3/1999 | Peterson |
| 5,882,323 | A | 3/1999 | Belkin |
| 5,919,148 | A | 7/1999 | Marko et al. |
| 5,929,782 | A | 7/1999 | Stark et al. |
| 5,940,992 | A | 8/1999 | Darby |
| 5,943,705 | A | 8/1999 | Sink |
| 5,951,499 | A | 9/1999 | Saringer et al. |
| 5,980,435 | A | 11/1999 | Joutras et al. |
| 6,007,500 | A | 12/1999 | Quintinskie, Jr. |
| 6,021,780 | A | 2/2000 | Darby |
| 6,027,468 | A | 2/2000 | Pick |
| 6,053,169 | A | 4/2000 | Hunt |
| 6,059,576 | A | 5/2000 | Brann |
| 6,076,266 | A | 6/2000 | Beckingham et al. |
| 6,093,162 | A | 7/2000 | Fairleigh et al. |
| 6,099,489 | A | 8/2000 | Herzberg et al. |
| 6,113,562 | A * | 9/2000 | Bonutti et al. ............ 602/20 |
| 6,142,964 | A | 11/2000 | Gilmour |
| 6,142,965 | A | 11/2000 | Mathewson |
| 6,155,994 | A | 12/2000 | Hubbard et al. |
| 6,179,747 | B1 | 1/2001 | Kelley |
| 6,179,800 | B1 | 1/2001 | Torrens |
| 6,184,797 | B1 | 2/2001 | Stark et al. |
| 6,196,956 | B1 | 3/2001 | Brown |
| 6,228,044 | B1 | 5/2001 | Jensen et al. |
| 6,267,742 | B1 | 7/2001 | Krivosha et al. |
| 6,296,595 | B1 | 10/2001 | Stark et al. |
| 6,371,123 | B1 | 4/2002 | Stark et al. |
| 6,384,755 | B1 | 5/2002 | Hayden |
| 6,409,691 | B1 | 6/2002 | Dakin et al. |
| 6,436,058 | B1 | 8/2002 | Krahner et al. |
| 6,485,447 | B1 | 11/2002 | Lavery et al. |
| 6,491,694 | B1 | 12/2002 | Orsak |
| 6,502,577 | B1 | 1/2003 | Bonutti |
| 6,503,213 | B2 | 1/2003 | Bonutti |
| 6,506,172 | B1 | 1/2003 | Hepburn et al. |
| 6,509,659 | B1 | 1/2003 | Carroll et al. |

OTHER PUBLICATIONS

Advertising materials from the Internet on Jun. 5, 1998 entitled: "Quadrant by Smith & Nephew DonJoy". "Entering a New Plane".
Advertising materials from the Internet on Jun. 5, 1998 entitled: "Make DonJoy's Quadrant Your First Choice for Effective Post-Operative Shoulder Treatment". "Quadrant Brace Specifications".
Advertising materials from the Internet on Jun. 5, 1998 entitled: "Ultraslingtm by DonJoy".
Neporent et al. "Weight Training for Dummies" 1997, p. 294.
Dynasplint Systems Inc., "Practitioner Information for Dynasplint LPS Orthosis—Knee Extension", date known but prior to Aug. 23, 1991.
Publication by UE Tech, Technology Meeting Human Needs, Rehabilitation Product Catalog, vol. 7, publication date unknown, but prior to Oct. 13, 1998.
Taber's Cyclopedic Medical Dictionary 16th Edition (1989) (#34), p. 521, definition of "distraction".

* cited by examiner

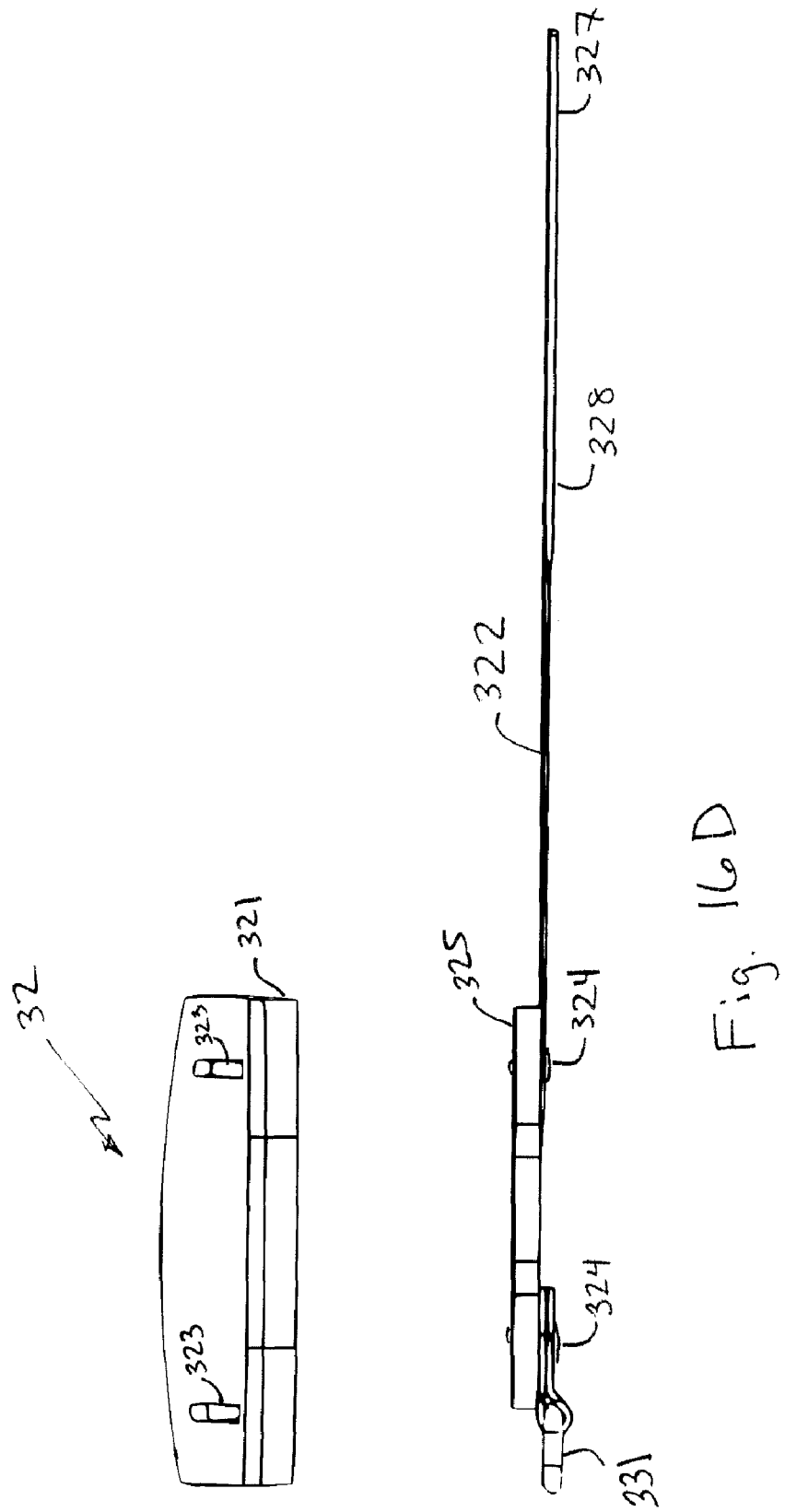

ORTHOSIS APPARATUS AND METHOD OF USING AN ORTHOSIS APPARATUS

CROSS REFERENCE TO RELATED APPLICATIONS

This application claims the benefit of U.S. Provisional Application No. 60/951,726, filed Jul. 25, 2007, and U.S. Provisional Application No. 61/033,786, filed Mar. 4, 2008. Both of the applications are incorporated by reference.

FIELD OF THE INVENTION

The present invention generally relates to orthoses for securing and rotating a human wrist and, more particularly, to an adjustable orthosis which can be used for stretching human tissue such as ligaments, tendons or muscles around a wrist and elbow joint.

BACKGROUND OF THE INVENTION

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Extension of the ankle would damage that joint. Other joints not only flex and extend, they rotate. The elbow joint, for instance, has supination and pronation which is rotation of the hand about the longitudinal axis of the forearm placing the palm facing up or facing down.

When a joint is injured either by trauma or by surgery, scar tissue can form, often resulting in flexion or extension contractures which can adversely affect the movement of the joint. For example, during supination or pronation of a patient's hand (palm facing upward or downward, respectively), the ulna and radius bones in the lower portion of the arm of the patient move relative to each other. During treatment of a patient for such an injury, it may be desirable to stretch viscoelastic body tissue connected with the ulna and radius bones and/or with the humerus in the arm of a patient in order to obtain a greater range of supination or pronation of the hand of the patient.

Injurious conditions can limit the range of motion of the joint, limiting flexion of the joint (in the case of an extension contracture) or limiting extension of the joint (in the case of a flexion contracture). It is often possible to ameliorate such conditions by use of a range-of-motion (ROM) orthosis. ROM orthosis secure certain bones involved with range of motion (for example, in the forearm) and mechanically induce movement. Such induced movement helps stretch the viscoelastic tissues to give the patient a greater range of mobility. In many instances, the patient can eventually enjoy a full range of movement.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. No. 6,599,263, entitled "Shoulder Orthosis;" U.S. Pat. No. 6,113,562, entitled "Shoulder Orthosis;" U.S. Pat. No. 5,848,979, entitled "Orthosis;" U.S. Pat. No. 5,685,830, entitled "Adjustable Orthosis Having One-Piece Connector Section for Flexing;" U.S. Pat. No. 5,611,764, entitled "Method of Increasing Range of Motion;" U.S. Pat. No. 5,503,619, entitled "Orthosis for Bending Wrists;" 5,456,268, entitled "Adjustable Orthosis;" U.S. Pat. No. 5,453,075, entitled "Orthosis with Distraction through Range of Motion;" U.S. Pat. No. 5,395,303, entitled "Orthosis with Distraction through Range of Motion;" U.S. Pat. No. 5,365,947, entitled "Adjustable Orthosis;" U.S. Pat. No. 5,285,773, entitled "Orthosis with Distraction through Range of Motion;" U.S. Pat. No. 5,213,095, entitled "Orthosis with Joint Distraction;" and U.S. Pat. No. 5,167,612, entitled "Adjustable Orthosis," all to Bonutti and herein are expressly incorporated by reference in their entirety.

What is needed in this art are range of motion devices that can stretch viscoelastic tissues to give the patient a greater range of mobility after an injury due to trauma or from surgery.

SUMMARY OF THE INVENTION

What is disclosed is a new and improved method and apparatus for use in effecting relative movement between a patient's hand and the bones in the patient's arm. The novel apparatus includes a main gear assembly having a lower cuff affixed therethrough for gripping a wrist and hand. The lower cuff can secure to a distal bone (i.e. the hand) and a medial bone (i.e. the forearm) of an appendage of a patient. The lower cuff centers the longitudinal axis of the forearm during rotational distal adjustment. The main drive assembly rotatable varies the extent of pronation and/or supination of the hand of the patient. A lower cuff arm connects, on one end, a vertical adjustment portion integral to the main gear assembly. The longitudinal axis of the patient's forearm is coincident with the longitudinal axis of the lower cuff arm. The lower cuff arm has a center cuff affixed on the lower cuff. The patient's arm rests on the center cuff during the use of the apparatus. The lower cuff arm is vertically adjustable relative to the fixed position of the rotatable drive assembly gripping the patient's hand. An adjustable upper cuff arm slideably attaches to an opposite end of the lower cuff arm at a point located behind the center cuff for gripping the patient's upper arm and holding it in a fixed position relative to the rotation of the hand. An upper cuff arm is adjustable both along the center axis of the lower cuff arm and along an angle of declination formed between the patient's upper arm and the lower cuff arm. The declination of the forearm relative to the upper arm is preferably adjustable and can be securely fixed at a desired angle by the medical practitioner to achieve the desired therapeutic effect. The interchangeability of the different parts of the orthosis of the present invention effectuates the device's assembly/disassembly and the interchangeability of parts to meet the patient's therapeutic needs.

Although the various embodiments of the orthosis described herein are preferably used to effect relative movement between bones in an arm of a patient, it is contemplated that an orthosis constructed in accordance with the present invention could be utilized to effect movement between bones in other portions of a patient's body. Of course, the size and/or the relationship of various components of the orthosis presented herein may be modified to adapt the orthosis for use with other portions of a patient's body.

In accordance with a further object of the invention, an orthosis apparatus is described that rotates (i.e. pronates and supinates) a forearm about a forearm axis. The orthosis apparatus includes an arcuate member, a means for rotating the arcuate member, and a means for aligning the arcuate member. The arcuate member is configured to at least partially surround the forearm, wrist, or hand axis. If the arcuate member is a ring, then the arcuate member fully can encircle the forearm, wrist, or hand. For purposes of the instant application, the distal end of the forearm includes the hand, the wrist, and forearm. The arcuate member is configured to be fixed to the forearm by suitable means such as a grip or a cuff. The arcuate member defines an arcuate member axis which is the center of rotation of the arcuate member. For a circular or partial circular arcuate member, the arcuate member axis is located at the center of arcuate member. The means for rotating the arcuate member about the arcuate member axis pronates and supinates the forearm held by the arcuate member. In order to rotate the forearm with minimum stress to the forearm, the axis of the arcuate member should be aligned with the forearm axis. The forearm axis the axis about which the forearm rotates from a pronated to a supinated state. The means for aligning the arcuate member axis with the forearm axis moves the arcuate member in relation to the forearm to align the two axes.

In accordance with a further object of the invention, the means for rotating the arcuate member includes an array of gear teeth and a drive gear. The array of gear teeth is disposed about the arcuate member. The gear teeth can be on the periphery or alternately on the inside of the arcuate member. The drive gear communicates with the gear teeth. The drive gear rotates the arcuate member about the arcuate member axis by rotating the arcuate member.

In accordance with a further object of the invention, the means for aligning the arcuate member axis with the forearm axis includes a track. The track is not parallel to the forearm axis. The arcuate member or an interconnecting piece travels on the track to move the arcuate member in relation to the forearm axis.

In accordance with a further object of the invention, the orthosis apparatus can include further a means for isolating the forearm axis in a given plane and a means for maintaining the arcuate member axis in the given plane when the means for aligning the arcuate member is operated. By fixing the forearm in space and then moving the arcuate member in a plane parallel to the forearm, the process of aligning the forearm axis and the arcuate member axis becomes simpler as the number of variables (i.e. only one axis versus two or three) needs to be adjusted. The means for isolating the forearm axis in a given plane includes a beam running parallel to the forearm axis and connected to the forearm. Generally, the forearm is rested on the beam or a pad on the beam until the wrist or hand is cuffed to the arcuate member. The means for maintaining the arcuate member axis in the given plane includes a track. The track may be disposed in the plane or can be disposed in a position parallel to the given plane. The arcuate member travels along the track during the aligning step.

In accordance with a further object of the invention, the arcuate member defines a plane and the plane is orthogonal to the forearm axis. By placing the arcuate member perpendicular to the forearm axis, the arcuate member axis and the forearm axis remain aligned throughout rotation of the arcuate member.

In accordance with a further object of the invention, the orthosis apparatus includes a means for coplanar aligning the arcuate member axis and the forearm axis. Coplanar aligning means to align (i.e. overlap linearly) the two axes while keeping the two axes in the same plane. The means for coplanar aligning the arcuate member axis and the forearm axis can include a beam fixed parallel to the forearm axis and a track disposed perpendicular to the beam and the forearm axis. The track is connected to the beam. The beam is preferably a lower cuff arm. The arcuate member travels on the track. The arcuate member axis is aligned parallel to said beam. This arrangement makes the alignment of the two axes much easier because there is only one variable to be adjusted during the aligning step.

In accordance with a further object of the invention, a lower cuff arm for an orthosis apparatus is provided. The lower cuff arm is a beam having a proximate and a distal portion. The proximate portion is configured to support a forearm. The distal portion is declined from the proximate portion. The declined portion has two advantages. First, the declined distal portion provides room for the arcuate member to travel and to be aligned. Second, the declined distal portion allows for the wrist to be bent as the arm is inserted into an upper cuff and then a lower cuff.

In accordance with a further object of the invention, distance that the distal portion declines from the proximate portion equals a distance that the arcuate member to be connected to the distal portion is to travel when the axes are being aligned.

In accordance with a further object of the invention, the distal portion of the lower cuff arm has a length that allows a hand of a patient to be inserted into the arcuate member. This length allows the patient to bend their wrist to fit into the lower cuff, especially when an upper cuff is connected to proximate portion of the lower cuff arm.

In accordance with a further object of the invention, a protective plate can be connected to arcuate member of the orthosis apparatus in order to provide clearance for a knob operating the arcuate member.

In accordance with a further object of the invention, a spring can be disposed on an axle of the drive gear. The spring provides tension on the drive gear and inhibits its rotation. In this way, the spring prevents unintentional rotation of the orthosis apparatus. In particular, the spring is heavy enough to prevent the forearm's own natural tendency to move to a neutral position when being stretched. In other words, the spring helps to hold the forearm in a stretch, pronated or supinated position.

In accordance with a further object of the invention, a method for performing an orthosis of a forearm is taught. The first step of the method is providing an arcuate member having a central arcuate member axis. The next step is fixing (i.e. preventing from moving) a forearm axis of a forearm of a patient while allowing rotation of the forearm about the forearm axis. The next step is aligning the arcuate member axis with the forearm axis by moving the arcuate member in relation to the forearm of the patient. The next step is fixing a hand of the patient to the arcuate member. The next step is rotating the arcuate member about the arcuate member axis. By following this procedure, the axes of the arcuate member and the forearm are aligned and the forearm is placed under the least unintentional stress during the orthosis of the patient's forearm.

The method may include isolating the forearm of the patient in a given plane during the fixing step and moving the arcuate member in the given plane during the aligning step. By keeping the arcuate member in the same plane as the forearm the number of spatial variables to be adjusted during the aligning step is minimized.

The invention will next be described in connection with certain illustrated embodiments. It should be understood that various changes and modifications can be made by those skilled in the art without departing from the spirit or scope of the invention.

BRIEF DESCRIPTION OF THE DRAWINGS

The accompanying figures, where like reference numerals refer to identical or functionally similar elements throughout the separate views, serve to illustrate various embodiments and to help explain various principles and advantages of the present invention. A more complete understanding of the invention will be more readily understood by reference to the following detailed description when considered in conjunction with the accompanying drawings wherein:

FIG. 16D is a bottom side view of the lower cuff shown in FIG. 16A.

DETAILED DESCRIPTION OF THE INVENTION

Briefly, what is disclosed is a new and improved method and apparatus for use in effecting relative movement between a patient's hand and the bones in the patient's arm. The novel apparatus includes a main gear assembly having a lower cuff affixed there through for gripping a wrist and hand. The lower cuff centers the longitudinal axis of the forearm during rotational distal adjustment. The main drive assembly rotatably varies the extent of pronation and/or supination of the hand of the patient. A lower cuff arm connects, on one end, a vertical adjustment portion integral to the main gear assembly. The longitudinal axis of the patient's forearm coincident with the longitudinal axis of the lower cuff arm. The lower cuff arm has a center cuff affixed thereon upon which the patient's arm rests during the use of the present apparatus. The lower cuff arm is vertically adjustable relative to the fixed position of the rotatable drive assembly gripping the patient's hand. An upper cuff arm slideably attaches to an opposite end of the lower cuff arm at a point located behind the center cuff for gripping the patient's upper arm and holding it in a fixed position relative to the rotation of the hand. The slideable upper cuff arm is adjustable both along the center axis of the lower cuff arm and along an angle formed between the patient's upper arm and the lower cuff arm. The declination of the forearm relative to the upper arm is adjustable and is fixable at a desired angle by the medical practitioner to achieve the desired therapeutic effect. The interchangeability of the different parts of the orthosis of the present invention effectuates the device's assembly/disassembly and the interchangeability of parts to meet the patient's therapeutic needs.

Although the various embodiments of the orthosis herein will be described in relation to effecting relative movement between bones in an arm, it is contemplated that an orthosis constructed in accordance with the present invention could be utilized to effect movement between bones in other portions of a patient's body.

Figure 17:
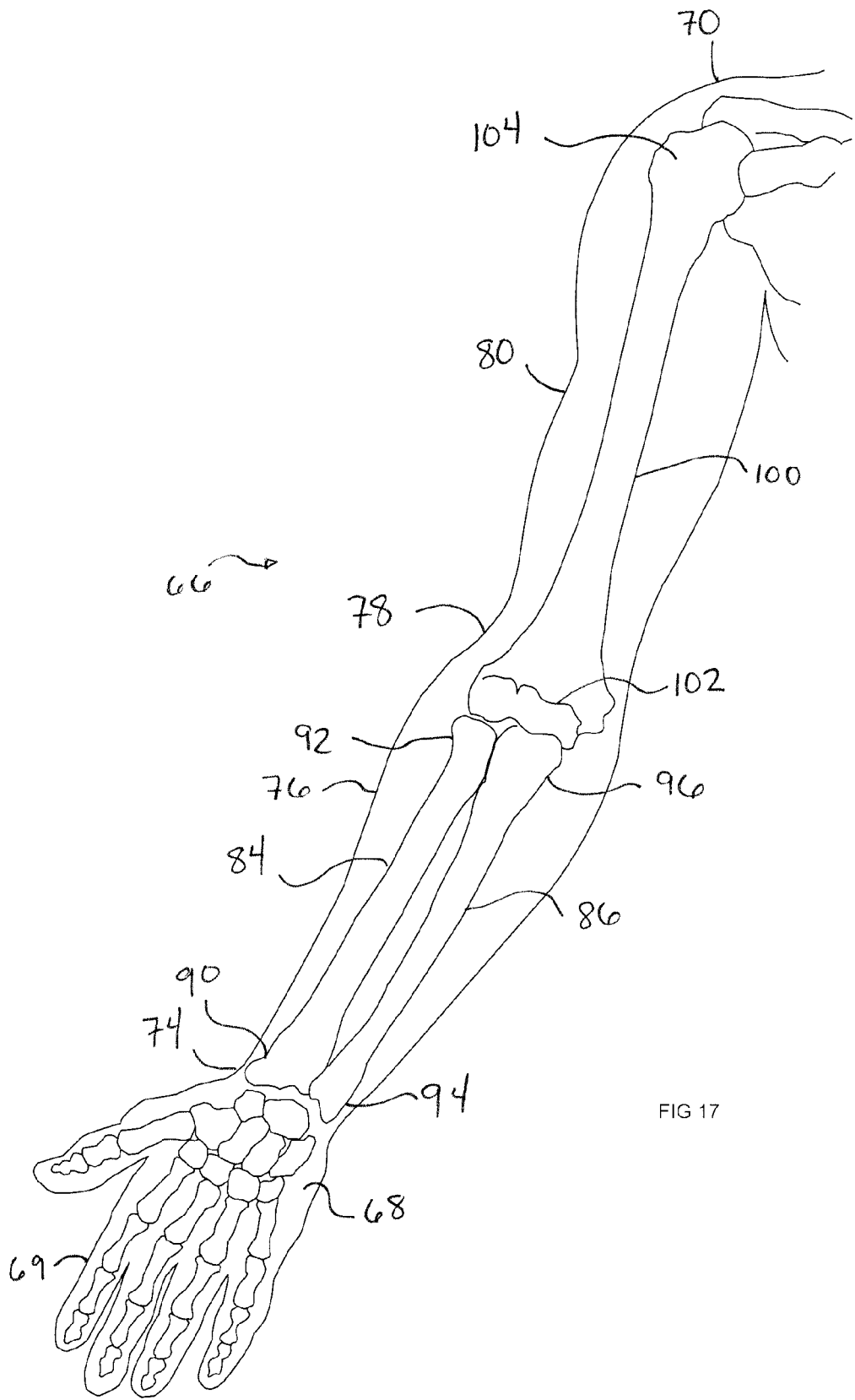
FIG. 17 is a partial diagrammatic and partial schematic front side sectional view of an arm of a patient according to the prior art.

At the onset hereof, attention is briefly directed to FIG. 17. FIG. 17 is an illustration of various aspects of the anatomy of a right anterior arm of a patient. The illustrated anatomy is pertinent to the discussion of the present orthosis. Although the present orthosis will find its intended uses with either the right or left arm of a patient, only a description of pertinent aspects of the anatomy of the right arm is provided. Further, the present orthosis will find its intended uses with the anatomy of non-human species as well.

With reference now being briefly made to FIG. 17, a patient's right arm 66 extends between a hand 68 and shoulder 70 of the patient. The right arm includes a wrist 74, a lower portion or forearm 76, an elbow 78, and an upper portion 80. The upper portion 80 of the arm extends between the shoulder 70 and elbow 78. The upper portion 80 of the arm 66 includes the humerus bone 100. The humerus 100 has a distal end portion 102 which cooperates with the proximal end portions 92 and 96 of the radius 84 and ulna 86, respectively. In addition, the humerus 100 has a proximal end portion 104 which cooperates with the shoulder 70. The lower portion or forearm 76 extends from the elbow 78 to the wrist 74. The wrist 74 is the region where the hand 68 is joined with the lower portion 76 of the arm 66. The elbow 78 is the region where the lower portion 76 of the arm 66 and the upper portion 80 are joined. The lower portion 76 of the arm includes a radius bone 84 and an ulna bone 86. The radius has a distal end 90 at the wrist 74. The radius 84 has a proximal end 92 at the elbow 78. Similarly, the ulna 86 has a distal end 94 at the wrist 74. The ulna 86 has a proximal end 96 at the elbow 78.

Pronation of the hand 68 occurs when the hand 68 is turned so that the palmar or anterior side of the hand 68 and wrist 74 face downward and the opposite or posterior side of the hand 68 and wrist 74 face upward. Supination of the hand 68 occurs when the hand 68 is turned so that the palmar or anterior side of the hand and wrist face upward and the opposite or posterior side of the hand and wrist face downward. During supination and pronation of the hand, the radius 84 and ulna 86 move relative to each other. As will be discussed herein in further detail, the present orthosis grips the wrist 74 and hand 68 while securing upper portion 80 of the arm 66 to isolate movement to the radius 84 and ulna 86 during pronation and/or supination of the hand 68.

It should be understood that, although the foregoing explanation has been in conjunction with the right arm 66 of a patient, the present orthosis is equally usable with the left arm. It should also be understood that the "patient" does not have to be a human patient as the present invention will also find its intended uses in the fields of veterinary sciences and research. The present orthosis may be used with a portion of a patient's body other than an arm. Of course, the size and/or relationship of various components of the orthosis presented herein may be modified, enlarged, or miniaturized, to adapt the present orthosis for use with other portions of a human or non-human patient's anatomy. Such modifications are intended to be readily encompassed within the scope of the claims appended hereto.

Figure 1:
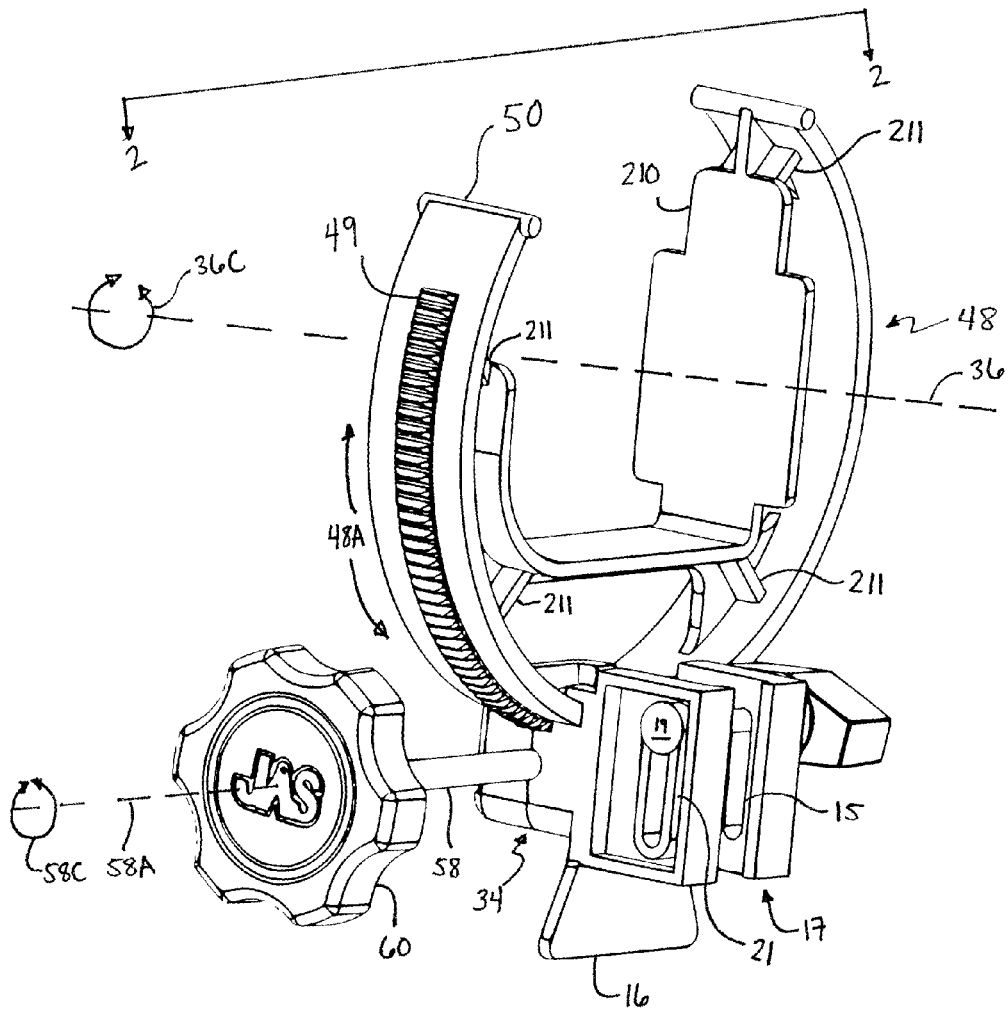
FIG. 1 is a right-rear oblique view of a main gear assembly according to the invention.
Figure 2:
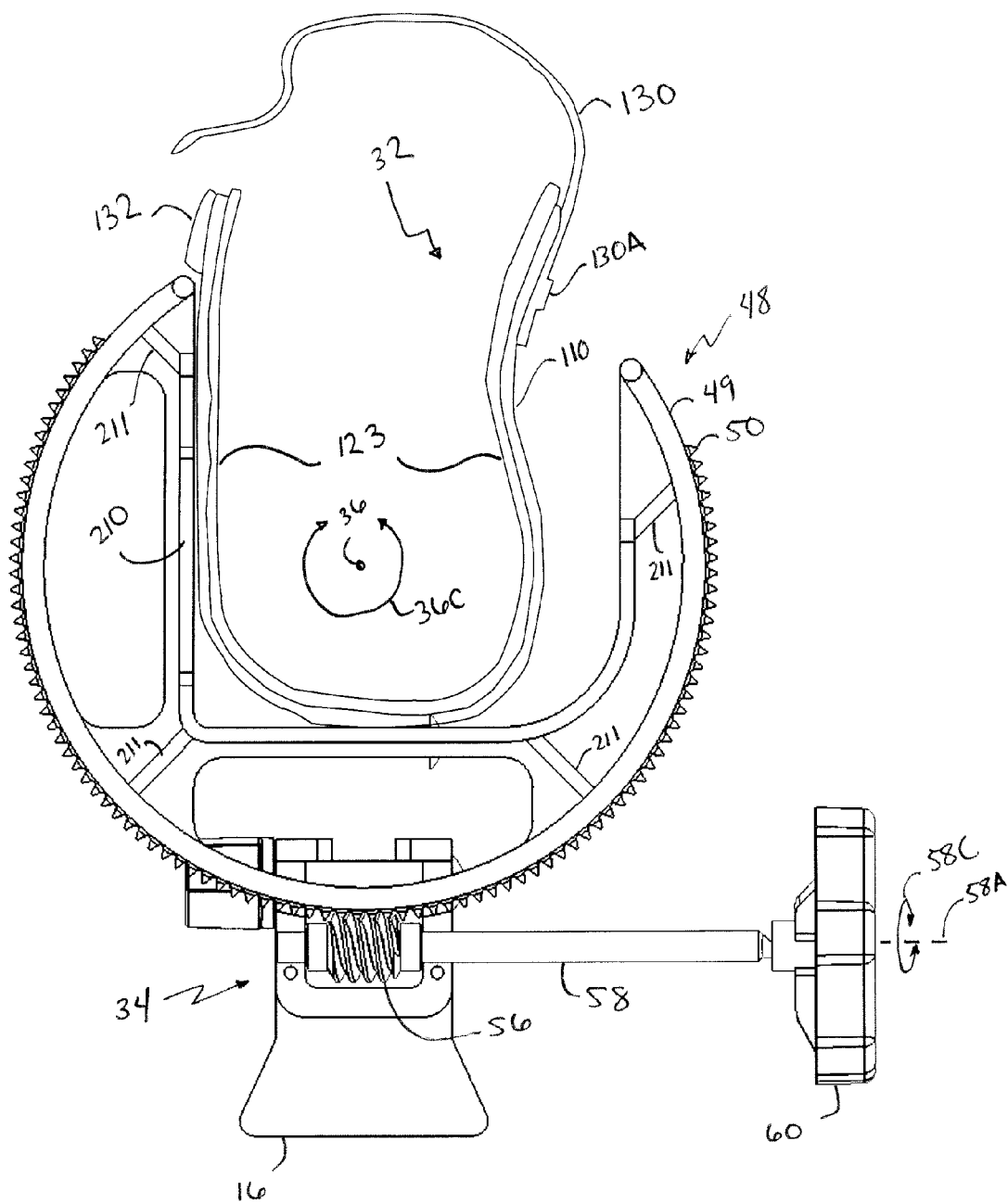
FIG. 2 is a front sectional view of the main gear assembly shown in FIG. 1 taken along line 2-2.

Attention is respectfully directed to FIGS. 1 and 2 jointly, which both illustrate an embodiment of the main gear assembly of the present orthosis. FIG. 1 is an oblique view of the main gear assembly 48. FIG. 1 illustrates various aspects such as the protective plate 16, knob 60 and shaft 58, vertical adjustment portion 17 to which a lower cuff arm attaches, and the row of gear teeth 49 positioned along one side of an arcuate member 50. FIG. 2 is a front side view of the embodiment shown in FIG. 1, taken along the line 2-2 of FIG. 1. FIG. 2 better illustrates pertinent aspects of the drive assembly 34. FIG. 2 illustrates the worm gear 56. FIG. 2 shows various components of lower cuff 32 for securing a patient's hand, and the fixation points 211 that secure a cuff support plate 210 to an inner side of the arcuate member 50. The combination of FIGS. 1 and 2 serve to better illustrate the various aspects of the main gear assembly 48 of the present orthosis.

Figure 13:
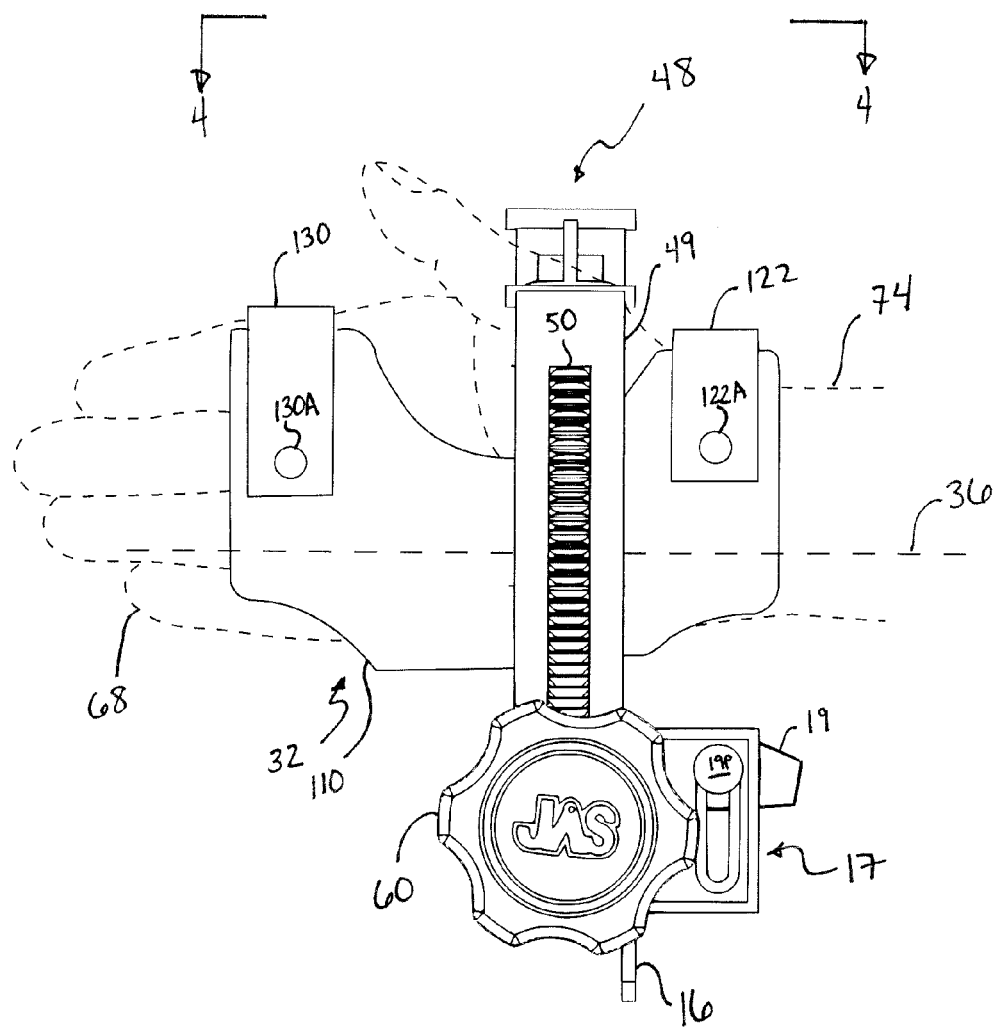
FIG. 13 is a partial left side view of the orthosis shown in FIG. 12 with the patient's hand secured in lower cuff.
Figure 14:
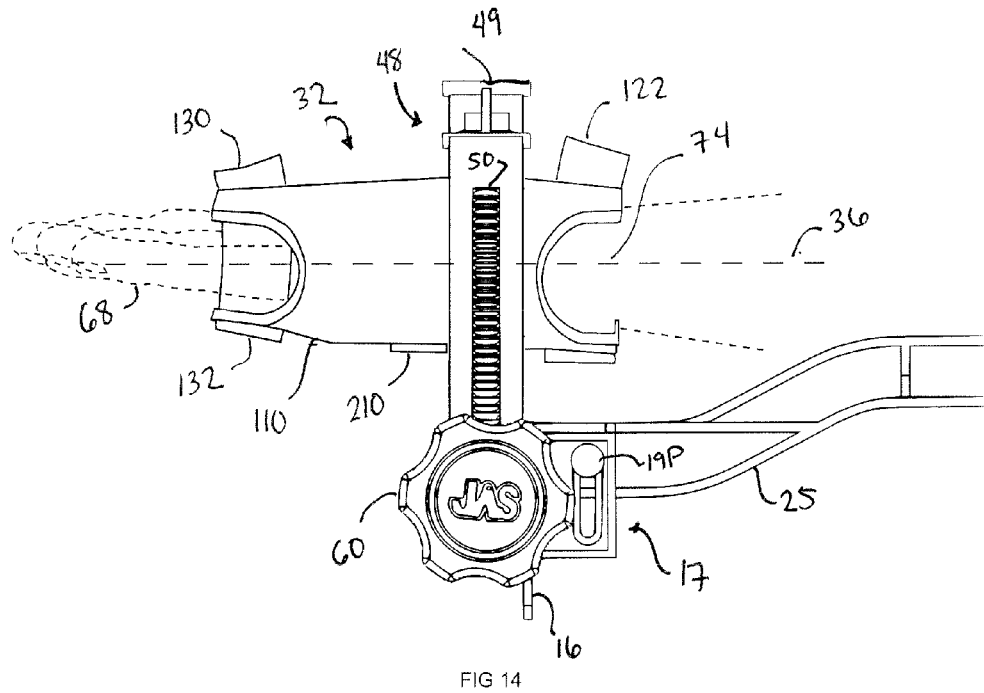
FIG. 14 is a left-side view of the orthosis shown in FIG. 13 with the patient's hand in a supinated position, taken along the line 4-4 of FIG. 13.
Figure 15:
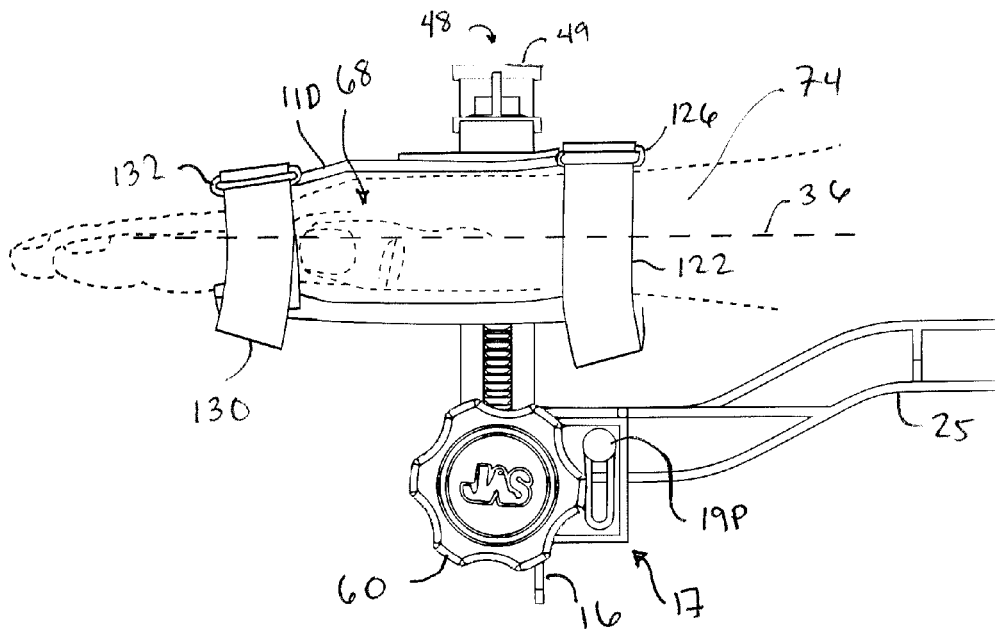
FIG. 15 is a left-side view of the orthosis shown in FIG. 13 with the patient's hand in a pronated position.
Figure 16A:
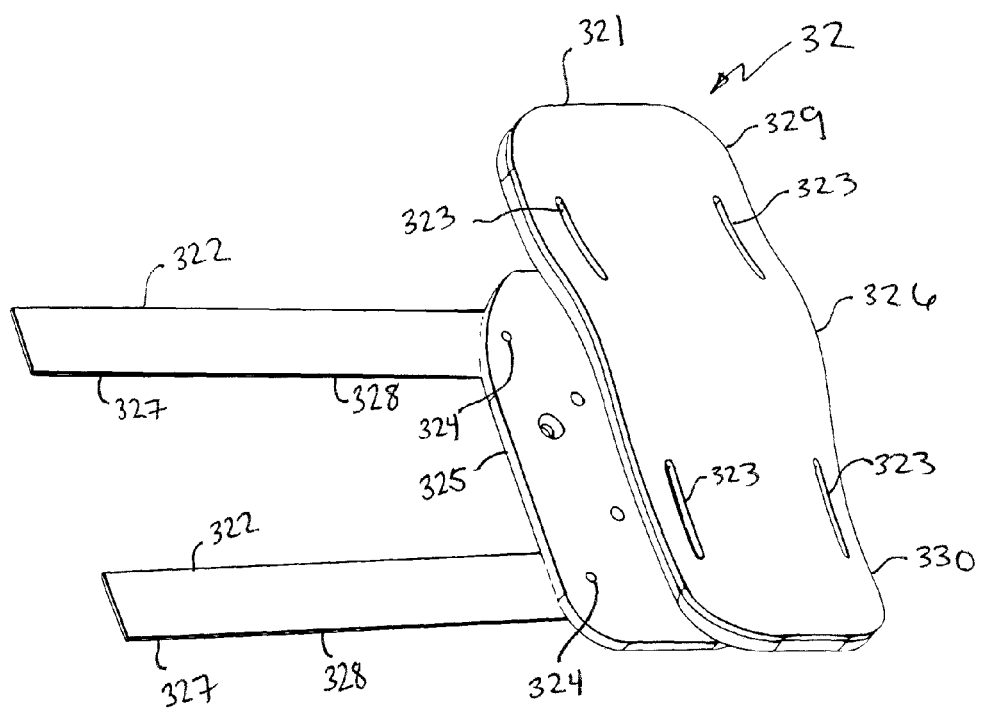
FIG. 16A is a front left bottom exploded oblique view of an embodiment of a lower cuff according to the present invention where the lower cuff is contoured to receive a palm of a patient's hand.
Figure 16B:
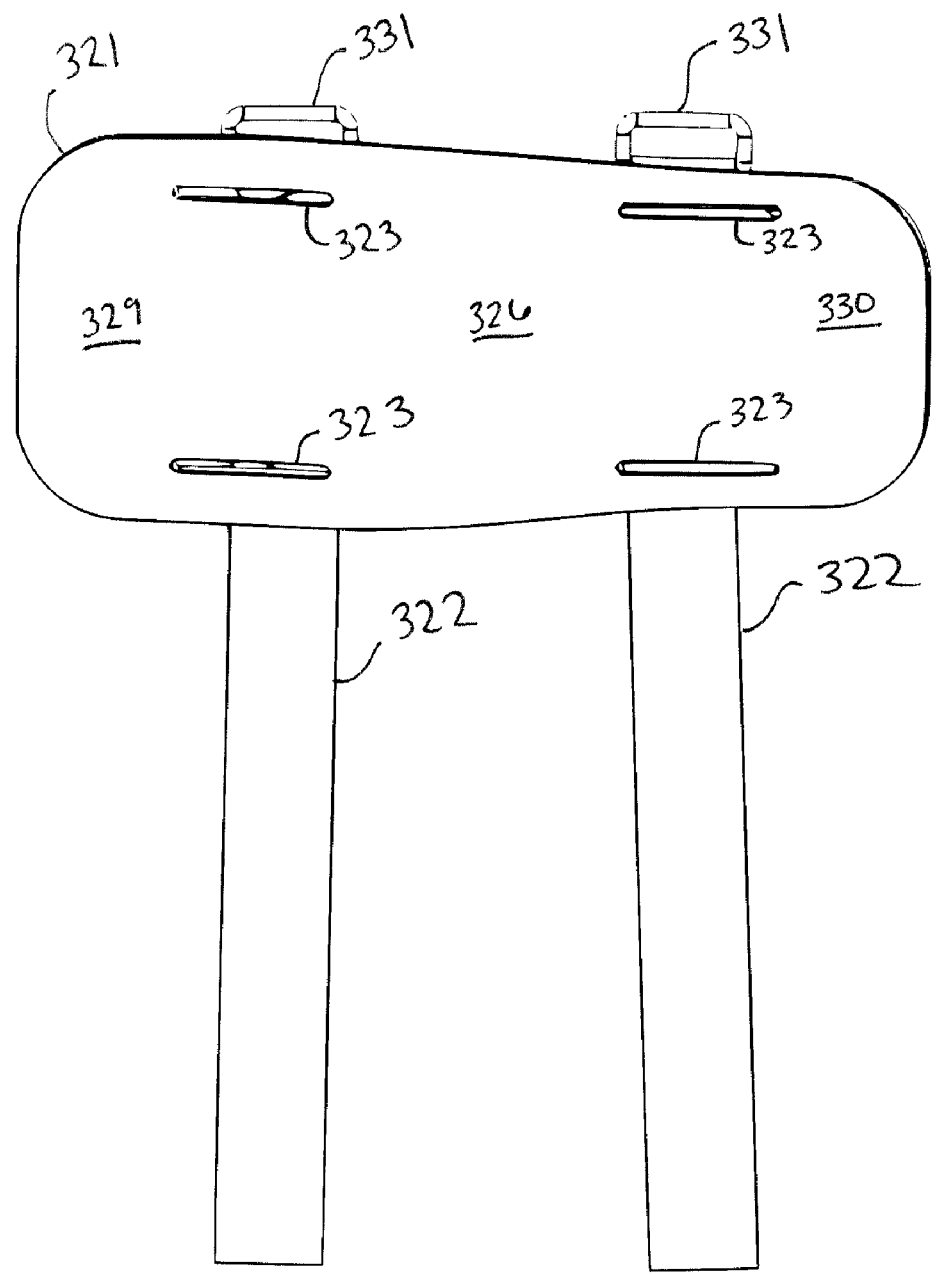
FIG. 16B is a front side view of the lower cuff shown in FIG. 16A.
Figure 16C:
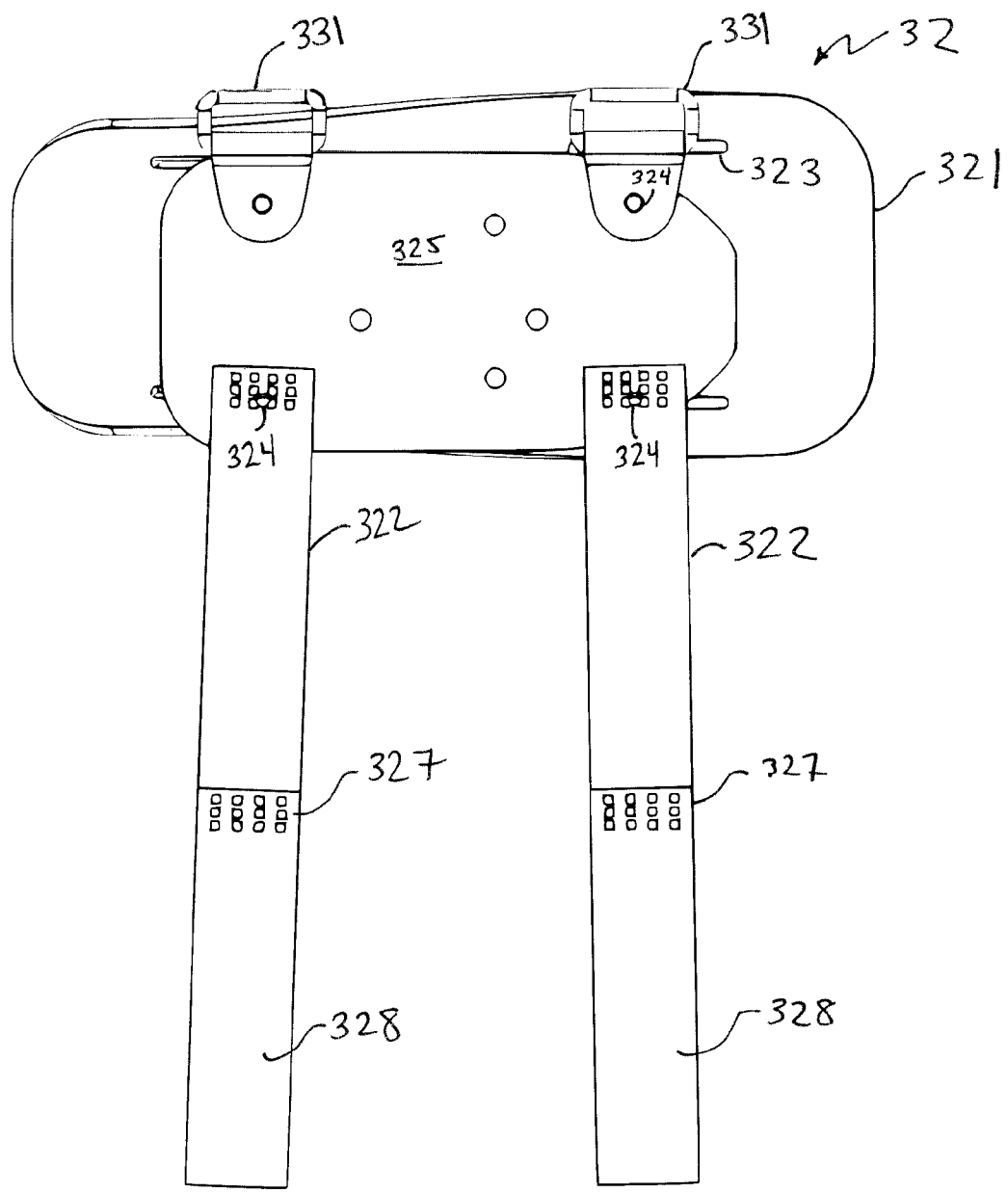
FIG. 16C is a rear side view of the lower cuff shown in FIG. 16A.
Figure 16E:
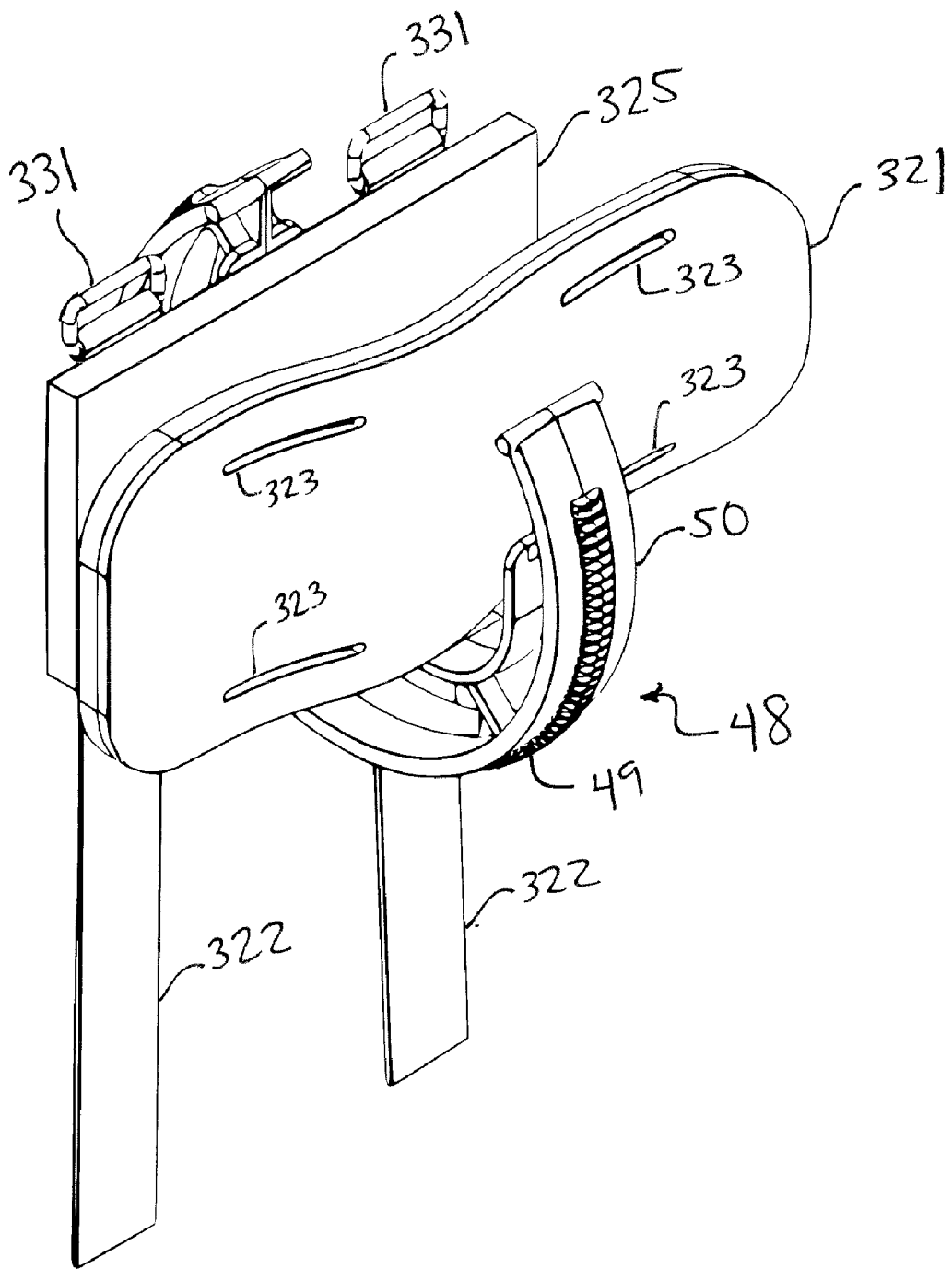
FIG. 16E is a top right front oblique view of the lower cuff shown in FIG. 16A attached to the main gear assembly.
Figure 16F:
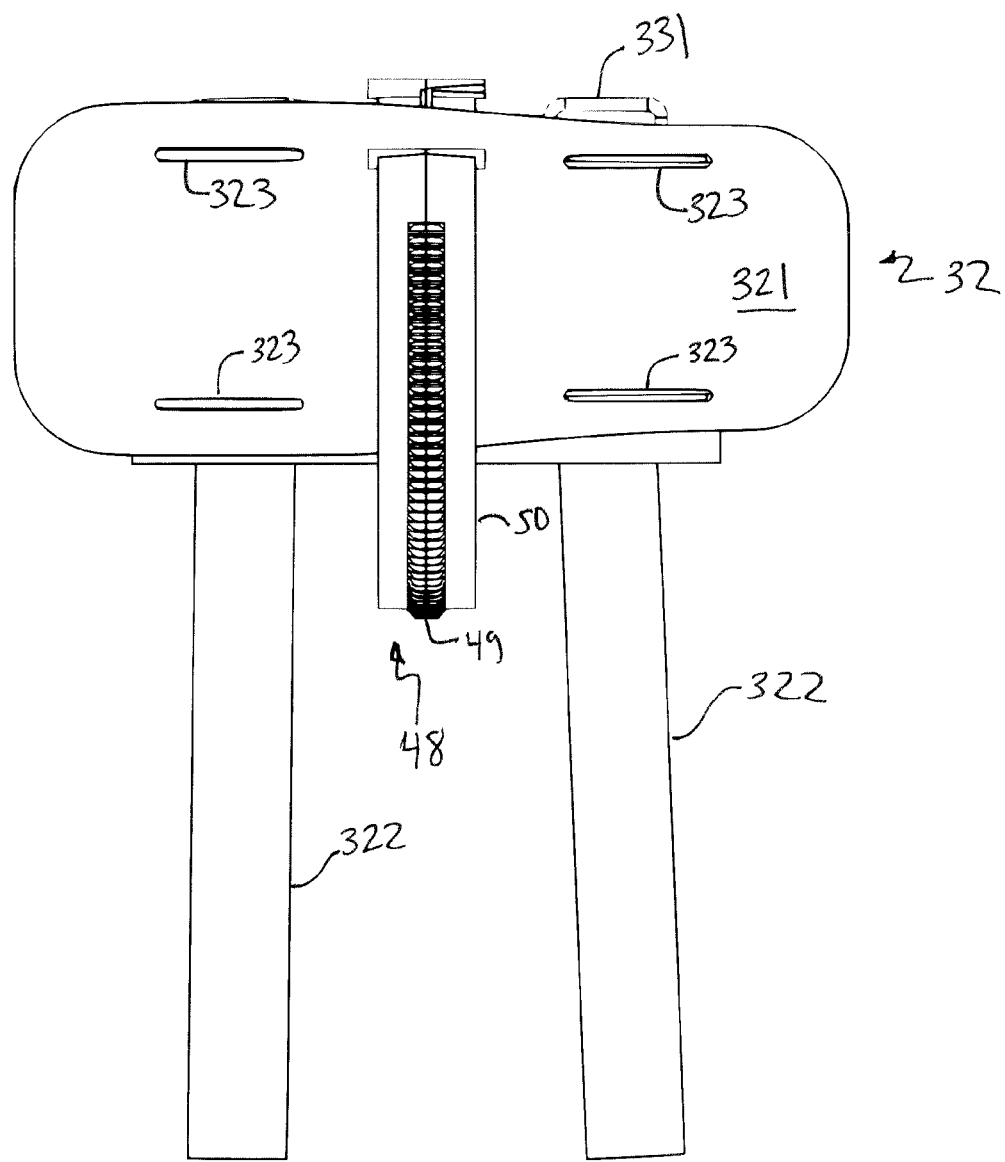
FIG. 16F is a front side view of the lower cuff shown in FIG. 16E.
Figure 16G:
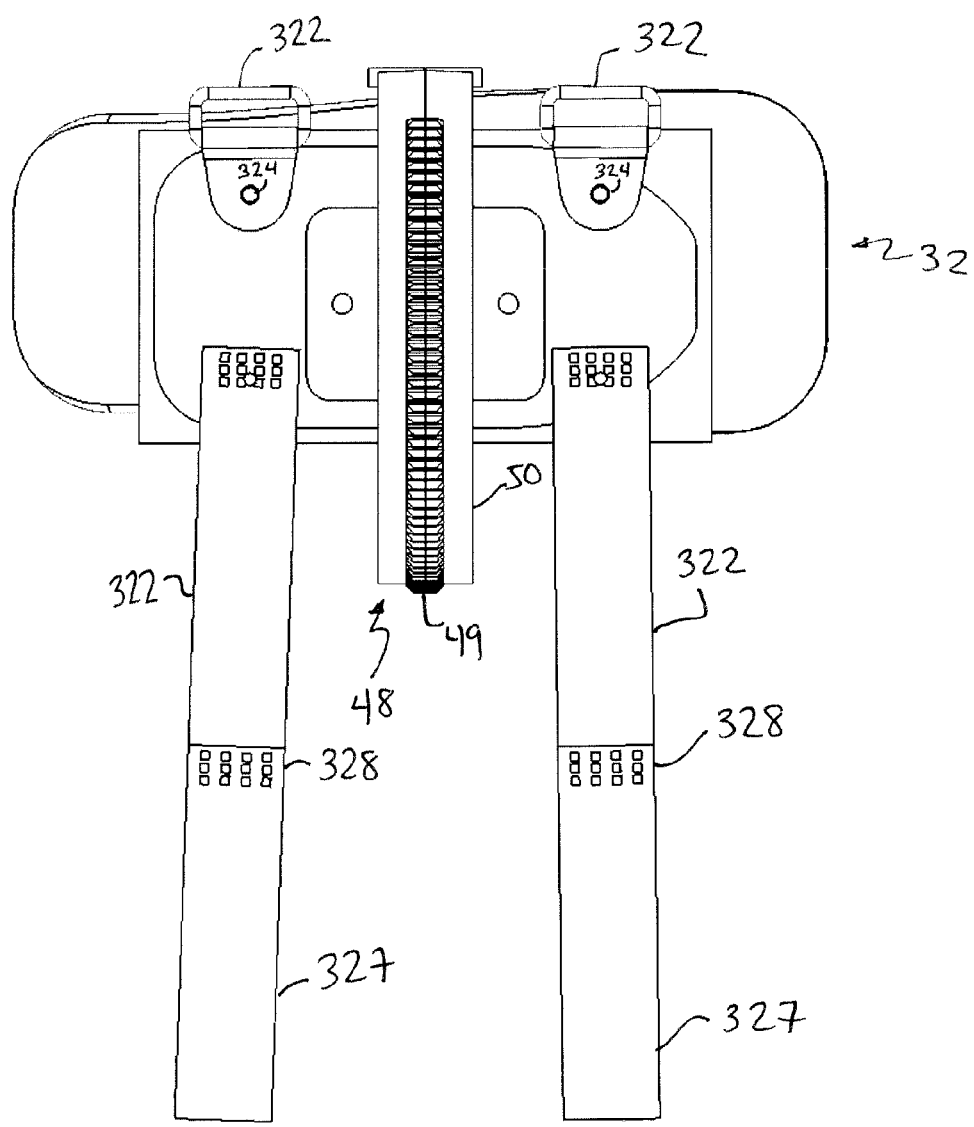
FIG. 16G is a rear side view of the lower cuff shown in FIG. 16E.

Generally, the main gear assembly 48 includes a rotatable arcuate member 50. The rotatable arcuate member 50 has a row of gear teeth 49 on an outer side thereof and a cuff support plate 210 fixed on an inner side thereof. Operationally, the patient's hand is securely strapped into the lower cuff 32. The lower cuff 32 is fixed to the cuff support plate 210 and is disposed inside the arcuate member 50. When the patient's hand has been strapped into lower cuff 32 and held in a fixed position to cuff support plate 210, the arcuate member 50 rotatably varies the extent of pronation and/or supination of the hand of a patient relative to the patient's arm, as will be discussed herein further in greater detail (FIGS. 13-15). The arcuate member 50 rotates in either a clockwise or counterclockwise direction 36C about a longitudinal center axis 36 by the rotation of shaft 58 about axis 58A by manually turning the knob 60.

In accordance with a feature of the invention, the main drive assembly 34 is operable to rotate the lower cuff 32 and the gripped portion of the wrist and hand of the patient about an axis 36. The lower cuff 32 firmly grips and transmits force from drive assembly 34 to the hand 68 and wrist 74. The axis 36, about which the lower cuff 32 and arcuate member 50 rotate, extends approximately midway between a sidewall 110 of the lower cuff 32 and axially through the wrist 74 and forearm 76 to the elbow 78. The axis 36 extends parallel to a longitudinal central axis of the lower cuff arm (not shown). When an arm 66 of a patient is held by the present orthosis, the axis 36 extends along the lower portion 76 of the arm 66 through the wrist 74 and elbow 78. Rotation of the lower cuff 32 by the rotational movement of the arcuate member 50 about the axis 36 varies the extent of pronation and/or supination of the hand of the patient.

As shown in FIG. 2, the lower cuff 32 generally comprises a semi-rigid sidewall 110, resilient foam lining 123, and one or more straps that are pulled tight to secure the hand inside the lower cuff. Lower cuff 32 is secured to a cuff support plate 210 on at least one side. The means by which the lower cuff is secured to cuff support plate 210 is not shown. In one embodiment, the sidewall 110 of lower cuff 32 is riveted to the cuff support plate 210. In other embodiments, ultrasonic welding is used. Alternatively or in combination, adhesives and other compounds secure the lower cuff 32 to the cuff support plate 210.

Figure 11:
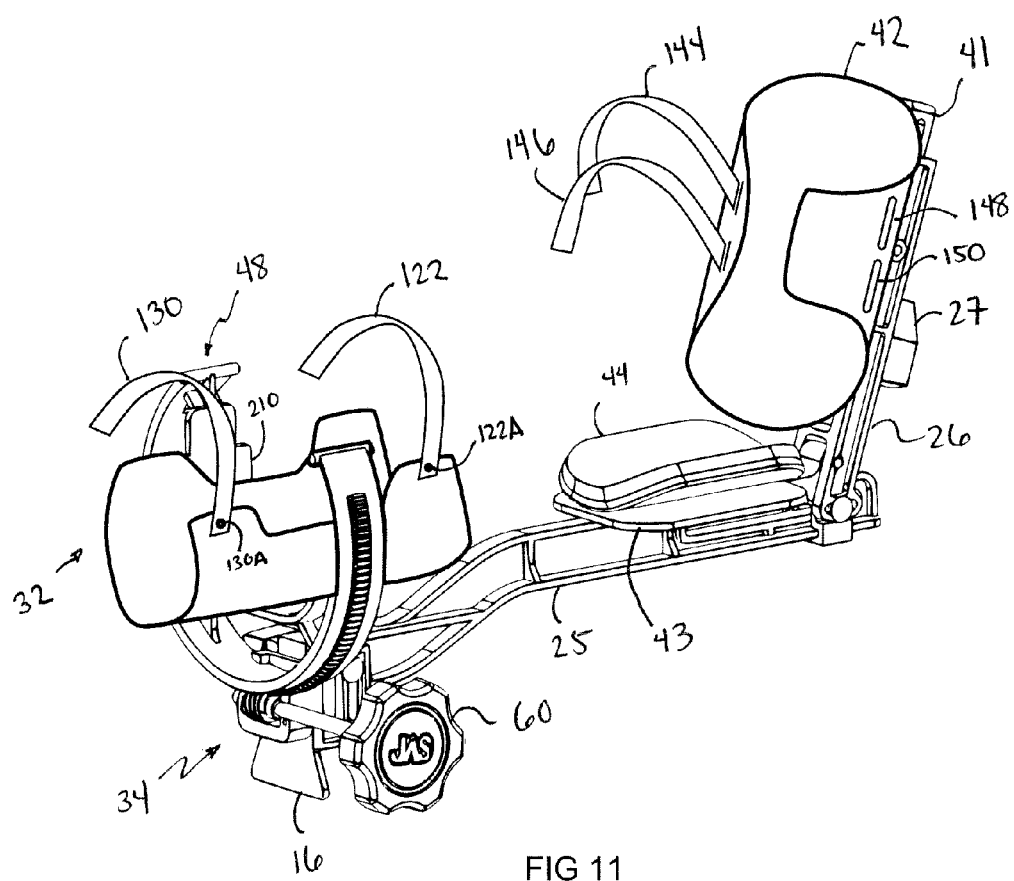
FIG. 11 is a front, right oblique view of the embodiment of the orthosis of FIG. 7 with a lower cuff, a center cuff, and an upper cuff attached.
Figure 12:
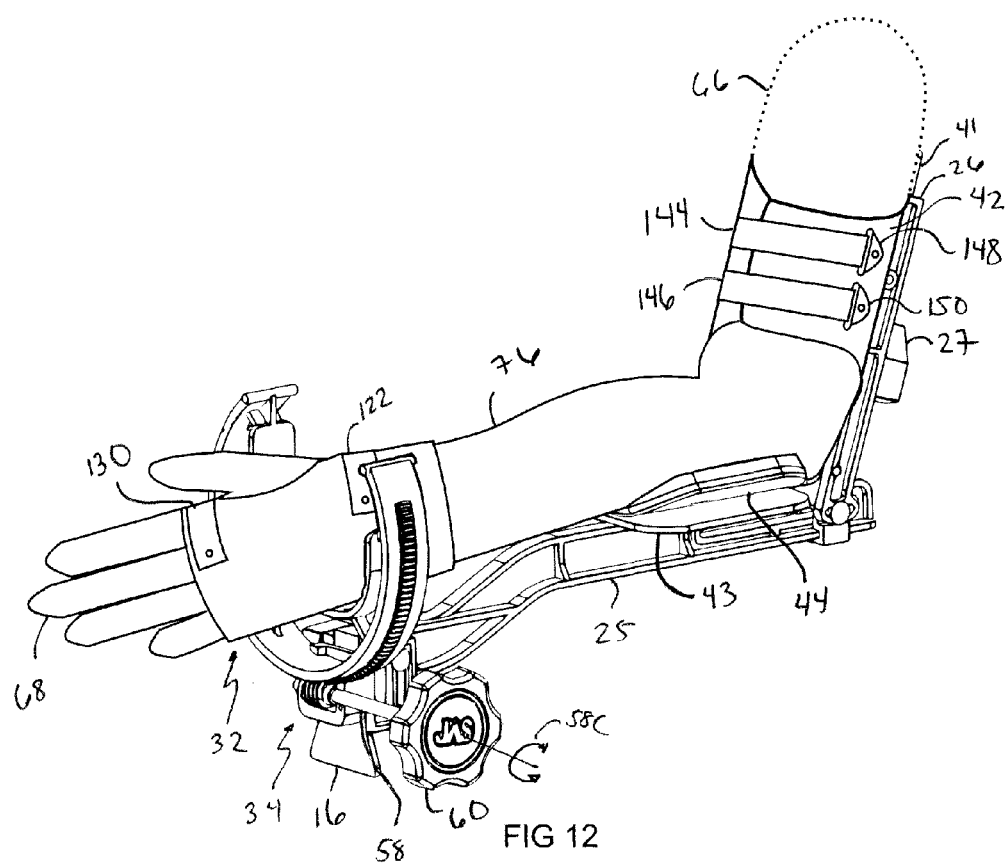
FIG. 12 is a top, front, right oblique view of the embodiment of the orthosis shown in FIG. 11 with a patient's lower arm resting on the center cuff, with upper arm secured by the upper cuff, and the wrist and hand secured by lower cuff.

As shown in FIGS. 11-13, the lower cuff 32 has two straps 122 and 130 for pulling the semi-rigid sidewall 110 material against the hand 68 thereby securing the patient's hand 68 and wrist 74 inside the cuff 32. A first strap 122 secures the forearm 76 or wrist 74 to the lower cuff 32. A second strap 130 secures the hand 68 to the lower cuff 32. Straps 122 and 130 are secured to the sidewall 110 of lower cuff 32 on one side by rivets 122A and 130A, respectively. In other embodiments, which are not shown in the figures, ultrasonic welding is used as an alternative or an addition to the rivets 122A and 130A. As shown in FIG. 15, the hand 68 is placed inside the lower cuff 32 and the straps 122 and 130 are pulled tight through a pair of rings 126 and 132, respectively. The rings 126 and 132 are mounted to an opposite outer portion of the sidewall 110 of the lower cuff 32.

As shown in FIGS. 13-15, the hand strap 130 is riveted to the sidewall 110 by rivet 130A. As shown in FIG. 12, the hand strap 130 extends over the patient's hand 68 between the thumb and index finger and through the ring 132 and pulled tight (FIGS. 13-15). The hand strap 130 presses the resilient foam lining 123 and sidewall 100 of the lower cuff 32 against the palmar or anterior side of hand and against the opposite or posterior side of the hand (back of the hand) to firmly grip the hand and hold it in place. Wrist strap 122 secures the patient's wrist 74. The wrist strap 122 presses a resilient foam lining 123 of sidewall 110 of lower cuff 32 firmly against the anterior side of wrist 74 and against the posterior side of the wrist 74 to firmly grip the wrist and hold the wrist in place. The portion of the lower cuff which grips the wrist 74 also grips the distal end portions 90 and 94 of the radius and ulna bones 84 and 86. Thus, both the hand 68 and wrist 74 are held firmly gripped inside the lower cuff 32. The distal ends of the radius and ulna are held against movement, in a direction perpendicular to axis 36, during rotation of the lower cuff in a direction circumferential to 36c. It should be understood that the distal ends of the radius 84 and ulna 86 can rotate somewhat during pronation and supination of the hand 68 and wrist 74.

In one embodiment, the lower cuff 32 is preferably formed as a singular piece of unitary construction generally comprising, a polymeric material having sufficient rigidity to be self-supporting and to apply adequate force against the hand 68 and wrist 74 while the patient's arm 66 remains relatively immobile. However, the sidewall 110 also has to be sufficiently flexible in order to enable the lower cuff 32 to be flexed to a limited extent and pressed firmly against the wrist and hand 68.

In another embodiment, the sidewall of lower cuff 32 is formed from a fabric material with sufficient rigidity to effectuate the intended purposes of the lower cuff 32. In addition, the sidewall 110 must accommodate hands of different sizes.

In another embodiment, the lower cuff 32 is detachable. Lower cuffs 32 having different sizes, shapes, or configurations can be substituted. Further, the axial extent of the sidewall 110 of the lower cuff could be reduced if it is desired to grip only the wrist.

In another embodiment, the sidewall 110 of the lower cuff 32 completely encloses the wrist 74 and has overlapping sidewall portions which connect to each other.

Although the embodiment illustrated in the figures shows the lower cuff 32 with a pair of straps 122 and 130 fixed to the sidewall 110 with a rivet 122A and 130A, other embodiments using glue, epoxy, or one or more other adhesives are envisioned. To be suitable, the adhesive must fasten the straps 122 and 130 to one side of the sidewall 110 of the lower cuff 32. In another embodiment, the straps 122 and 130 are secured to sidewall 100 by stitching, ultrasonic welding, or otherwise fixed to sidewall 110 during a manufacturing process.

Although the embodiment illustrated in FIG. 15 shows the straps 122 and 130 for the lower cuff 32 passing through a set of rings 126 and 132, an embodiment that is not illustrated connects the straps 122 and 130 to the sidewall with a hook and loop fastener such as those sold under the trademark VELCRO®. In another embodiment, the straps 122 and 130 are secured with one or more laces that secure the hand and wrist into the lower cuff when pulled tight and tied.

FIG. 16 shows another embodiment of a lower cuff 32. The lower cuff has a base plate 325. A palmer plate 323 overlies and is connected to the base plate 325. The palmer plate 323 is contoured to conform to the palm of the wearer. In particular, the palmer plate 323 includes a bump 326 that is received in the palm of the wearer. A finger area 329 and a thenar area 330 are relatively low compared to the bump 326. The finger area 329 receives the fingers of the patient. The thenar area 330 receives the thenar of the patient. The straps 322 are flexible. The straps 322 fold over the patients hand and through a respective slot 323. Each strap 322 has a hook 327 and loop 328 fastener. The strap is inserted through the respective slot 323 and folded on itself to close the fastener. Rivets 324 attach the straps 322 to the base plate 325.

With reference being made to the embodiment shown in FIGS. 1 and 2, cuff support plate 210 includes a three-sided fixture of sufficient rigidity held securely to an inner side of the arcuate member 50. The cuff support plate 210 is rigidly secured at a plurality of fixation points, collectively at 211. The fixation points 211 are either braces or spot welds that connect the cuff support plate 210 to the arcuate member 50 depending on the material with which the arcuate member and cuff support plate are constructed. Alternatively, the fixation points 211 are welded plastic, pressure fittings, or include an adhesive material. The fixation points 211 are sufficiently rigid to connect the cuff support plate 210 to an inner side of arcuate member 50 while the patient's hand is being gripped by lower cuff during rotation. Preferably, the arcuate member 50 and the lower cuff support plate 210 are of molded construction of plastic, ceramic, metal, or a composite material of sufficient durability, resiliency, and rigidity.

Figure 3:
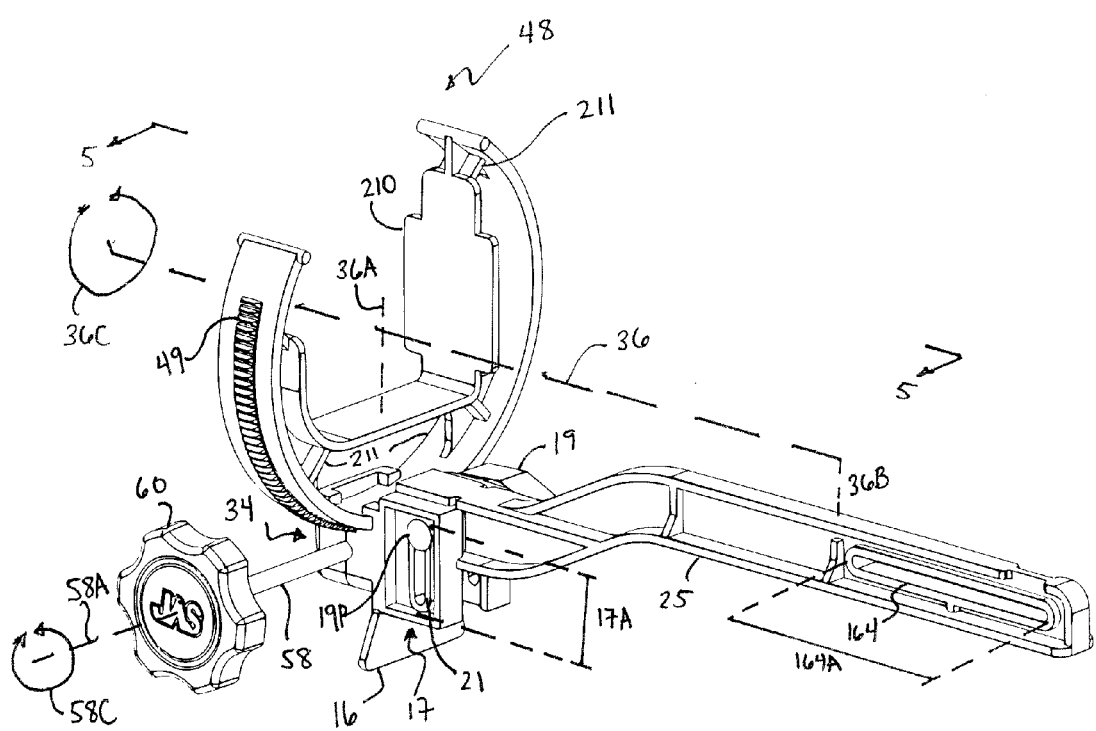
FIG. 3 is a top, right, rear oblique view of a first embodiment of the orthosis, which has a curved lower cuff arm connected to the main gear assembly shown in FIGS. 1-2.
Figure 4:
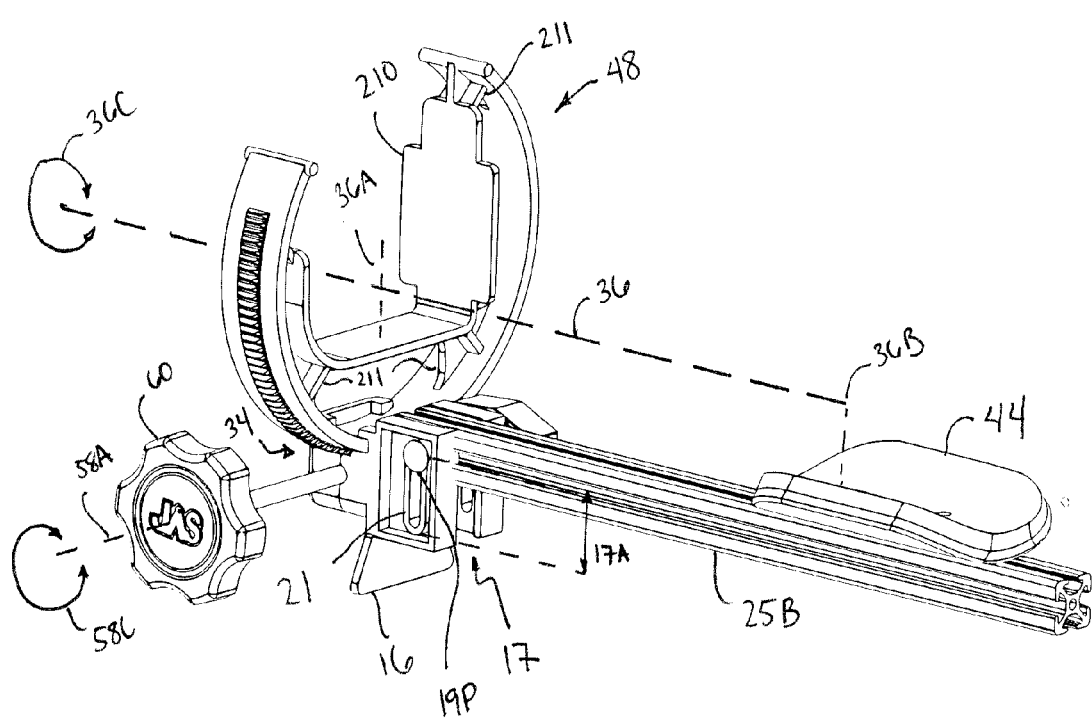
FIG. 4 is a top, right, rear oblique view of a second embodiment of the orthosis, which has a straight lower cuff connected to the main gear assembly shown in FIGS. 1-2.
Figure 7:
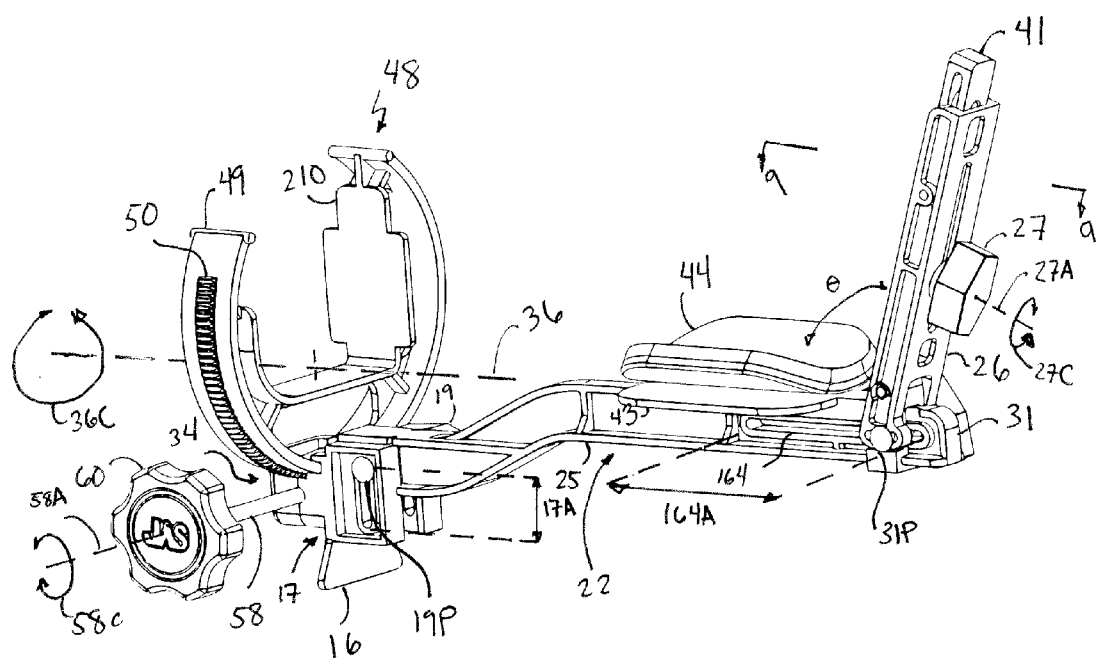
FIG. 7 is a top, right, rear oblique view of the embodiment of the orthosis shown in FIG. 3 attached to an upper cuff arm.

As shown in FIGS. 3-4 and 7, arcuate member 50 is rotatable about an axis of a lower cuff arm 25. The axis of the lower cuff arm 25 is coincident to longitudinal axis 36. The lower cuff arm 25 is secured to the main gear assembly 48 through a first vertical adjustment portion 17. The lower cuff arm 25 is centered in the vertical adjustment portion 17 by placing one end of the lower cuff arm 25 into the slot 15 in the direction indicated. The lower cuff arm 25 is pushed into slot 15 until an opening in the lower cuff arm (not shown) is in alignment with slot 21 through which pin 19 passes. With the passing of a securing pin 19 through slot 21, the lower cuff arm 25 is held in place. The securing of a lower cuff arm 25 to the first vertical adjustment portion 17 of the main gear assembly 48 will be discussed in further detail.

In an alternative embodiment, the lower cuff arm 25 is pushed through the vertical adjustment portion 17 in the direction of shown by 15 and extends forward of the main gear assembly 48 and is lockable into position along the longitudinal axis coincident with central axis 36. Alternatively, the lower cuff arm 25 is secured in the vertical adjustment portion 17 with a clamping or other pressure inducing mechanism such that the lower cuff arm 25 does not have to have a hole passing there through for receiving pin 15. Such a securing mechanism still allows for the vertical adjustment of the lower cuff arm 25 relative to the height of the lower cuff 32 while still holding the lower cuff arm 25 securely in place.

On an outer side of arcuate member 50 of main gear assembly 48 are a plurality of gear teeth, collectively at 49. The gear teeth of arcuate member 50 are physically engaged by a drive gear 56 housed inside drive assembly 34 which is disposed in meshing engagement with arcuate member 50. In the illustrated embodiment of the main drive assembly 34 of FIG. 2, the drive gear 56 is a worm. The terms "drive gear" "worm gear" and "worm" are used interchangeably throughout the application unless otherwise noted. The drive gear or worm 56 is rotatably mounted and fixedly connected to shaft 58. In this regard, drive gear 56 and shaft 58 can be a single unit, for example molded as one piece. A suitable knob 60 connected on an end of shaft 58 is manually rotated to operate the drive assembly 34. It is contemplated that the drive gear 56 mechanism of drive assembly 34 could have a different construction if desired as drive gears are well known in the arts. A spur gear is an alternate embodiment that is not shown. Alternatively, a motor could be connected to rotate the shaft 58 in order to operate the gearing mechanism of drive assembly 34. The drive gear 56 is rotated about an axis which extends perpendicular to and is offset from axis 36.

In an embodiment, an electric motor is mounted for actuation of drive gear 56. A battery provides electric power to the motor. Alternatively, the motor can be supplied with external power (i.e. an AC power source). A microprocessor controls the operation of the motor. The microprocessor and motor together can be used to cycle the device through supination and pronation; to rotate a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the drive gear 56 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

Turning the knob 60 in either a clockwise or counterclockwise direction (along circumference 58C) rotates shaft 58 about axis 58A. The rotation of the shaft 58 causes the worm gear 56 of drive assembly 34 to engage meshingly the gear teeth 49 of the arcuate member 50. Whenever the knob 60 is turned in one of the rotational directions circumferential to 58C, the arcuate member rotates about axis 36 in a first rotational direction along 36C. Conversely, whenever the knob 60 is turned in an opposite rotational direction, the arcuate member 50 rotates about the axis 36 in an opposite rotational direction. In such a manner, lower cuff 32 rotatably varies the extent of pronation and/or supination of the hand of the patient as will be further illustrated herein.

With reference to FIGS. 1 and 2, a protective plate 16 is advantageously provided as a support and further protects the drive assembly 34 from damage while in use. The protective plate 16 is made from a material that bears the weight of the orthosis while providing protection for drive assembly 34 and the bottom portion of the main gear assembly 48. The addition of the protective plate 16 advantageously enables the drive assembly 34 to be constructed of a light-weight more cost effective material. The height of the protective tab 16 is great enough to elevate the knob 60 above a surface on which the protective tab 16 rests. Preferably, at least an additional clearance (more than three centimeters) is provided to allow the knob 60 to be operated without the operator's fingers contacting the mounting surface. The protective tab 16 has a trapezoid shape with the longer base contacting the surface on which the orthosis rests. It may be desirable to mount the orthosis of the present invention securely to a fixed surface such as a chair, desk, or table. In this case, the protective plate 16 could be modified to have a tabbed end-bottom (or side) portion. The tabbed portion enables the main gear assembly 48 to be securely fastened to such a surface by either a screw or other fitting. Alternatively, the protective plate 16 could have one or more holes formed therethrough to facilitate the secure mounting of the present orthosis. Other means for fastening the present orthosis are envisioned.

The main gear assembly 48 is preferably of unitary molded construction. Alternatively, one or more components of the main gear assembly discussed above are individually manufactured and the parts of the present orthosis assembled in a cost effective manner. Cost effective construction and construction materials translates into lowered production costs which, in turn, mean cheaper, less expensive orthosis being presented to the patients. In addition, the inclusion of the protective plate 16 allows plastics to be used to construct the orthosis. Manufacturing involving plastic molds can greatly reduce the overall time required to produce the parts of the orthosis. This, also in turn, translates into more products being produced more quickly and more efficiently.

Figure 5:
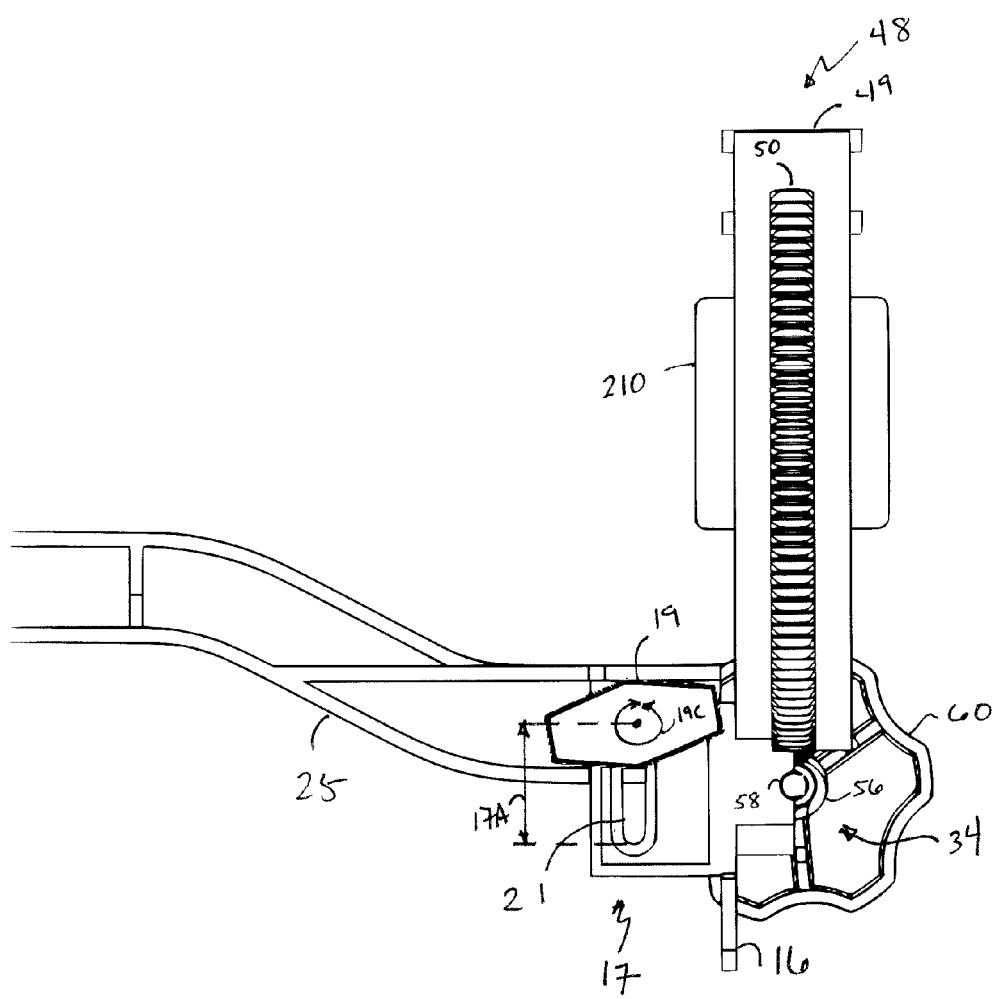
FIG. 5 is a partial, left-side sectional view of the embodiment of FIG. 3, taken along the line 5-5 of FIG. 3, which more fully illustrates the vertical adjustment portion of FIG. 3.
Figure 6:
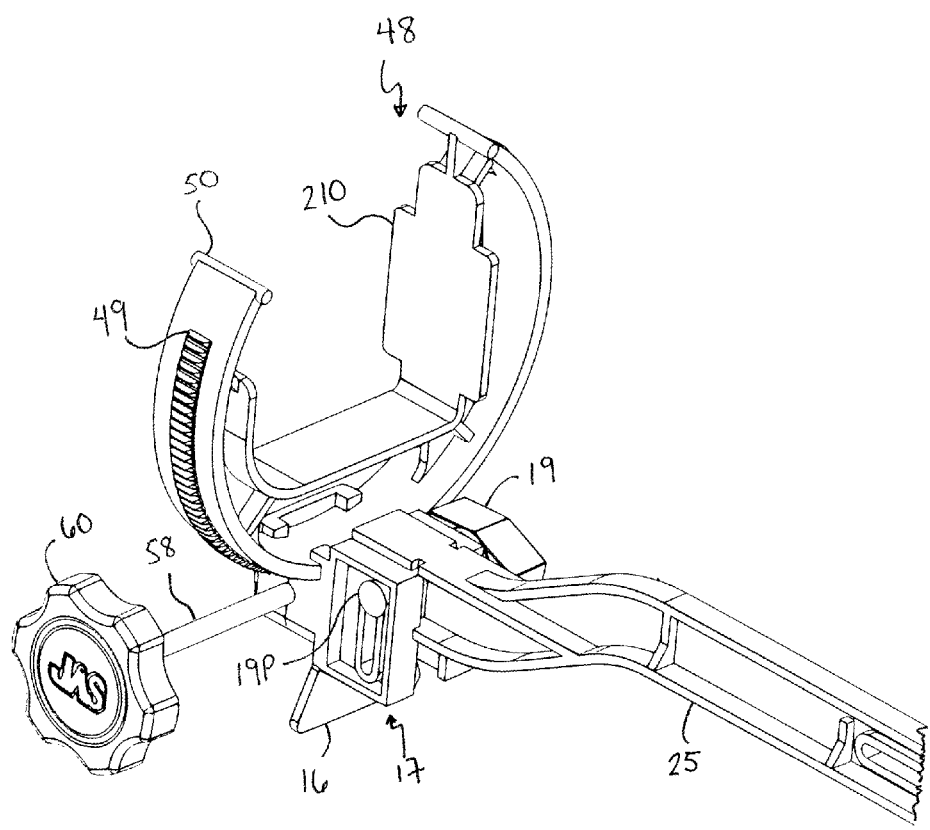
FIG. 6 is a partial, top, right, rear oblique view showing the embodiment shown in FIG. 3.

Attention is respectively directed to FIG. 3 which is a pictorial illustration of a first embodiment of the orthosis of the present invention showing the lower cuff arm 25 connected to the main gear assembly 48 of FIG. 1. Attention is also respectfully directed to FIGS. 5 and 6, which more fully illustrate the vertical adjustment portion 17 of FIG. 3.

The lower cuff arm 25 of the embodiment of FIG. 3 has a curved forward portion such that forearm can be raised relative to the position of the hand secured in the lower cuff 32 of main gear assembly 48. Depending on the degree of supination or pronation of the hand desired by the medical practitioner to meet the patient's specific needs, it may be desirable to employ the lower cuff arm having the curved configuration illustrated in FIG. 3. The lower cuff arm is further adjustable vertically by way of the vertical adjustment portion 17.

One end of the lower cuff arm 25 is fitted into the vertically adjustable first portion 17 of main gear assembly 48 by placement thereof into slot 15 (FIG. 1) and held securely in place by the pin 19P. The pin 19P passes therethrough to engage threadably suitable knob 19. The knob 19 is preferably threadably engaged and rotatable about the axis of the pin 19P in a direction circumferential to 19C (FIG. 6) such that whenever knob 19 is turned (for example in a clockwise direction) first vertical adjustment portion 17 clamps the lower cuff arm 25 into a fixed position. Conversely, whenever the knob 19 is rotated in a counterclockwise direction, the knob 19 threadably disengages pin 19P such that lower cuff arm 25 is loosened and manually adjusted vertically (up or down) in the direction of travel indicated at 17A. Whenever the lower cuff arm is adjusted downward in slot 15 (along the axis of 17a), the distance between the lower cuff arm and the central axis 36 (marked by the intersection of axis 36 with vertices 36A and 36B) increases, thereby lowering the lower cuff arm 25 relative to the main gear assembly 48. Whenever the lower cuff arm is adjusted upward in slot 15 (along axis of 17A), the distance between the lower cuff arm 25 and the central axis 36 (marked by the intersection of axis 36 with vertices 36A and 36B) decreases, thereby raising the lower cuff arm 25 relative to the main gear assembly 48. In such a manner, turning of knob 19 in one direction tightens height adjustment portion 17 clamping the lower cuff arm 25 in a fixed position in slot 15. Turning knob 19 in an opposite direction loosens the clamping action of adjustable portion 17, thereby enabling the raising or lowering vertical adjustment of lower cuff arm 25 in the direction indicated by axis 17A. The intended purpose of raising or lowering the lower cuff arm relative to the height of a central axis will become clearer herein further with regard to the explanation of the other figures provided.

As shown in FIG. 3, the lower cuff arm 25 of the embodiment includes a slot 164 for the slideable attachment thereto of one upper cuff arm assembly found in the art such as that disclosed in U.S. Pat. No. 5,848,979 to Bonutti et al., which is incorporated herein in its entirety by reference. An upper cuff arm assembly is attachable to an end of the lower cuff arm 25 opposing the main gear assembly 48. The upper cuff arm assembly grips the patient's upper arm and holds the patient's upper arm in a fixed position relative to the rotation of the hand. The upper cuff arm assembly is preferably telescopically adjustable along the center axis of the lower cuff arm and adjustable along an angle (shown in FIGS. 7-9) formed between the upper cuff arm and the lower cuff arm. The declination of the forearm relative to the upper arm is preferably adjustable and can be securely fixed at a desired angle by the medical practitioner to achieve the desired therapeutic effect. The upper cuff arm attachment is held in place by a pin secured through slot 164. Tightening or loosening the pin enables the elbow assembly to be slideably adjustable along lower cuff arm 25 in a direction coincident to axis 36. In such a manner, the embodiment of the orthosis with the slideably engaged assembly can be adjusted depending on the patient's physical or therapeutic requirements.

Attention is respectfully directed to FIG. 4 showing yet another embodiment of the orthosis of the present invention. In this embodiment, the main gear assembly 48 is as described with relation to the embodiment of FIG. 1. The drive assembly 34 functions by rotating the knob 60 to turn the shaft 58 about axis 58A in either direction along 58C. The lower cuff arm 25B of this embodiment differs from the lower cuff arm 25 of FIG. 3 in that this lower cuff arm is straight and has no curvature. The lower cuff arm 25B is straight horizontally along an axis coincident with axis 36. This may be preferable in those instances where the medical practitioner has determined that the patient's particular therapeutic needs do not require the use of a curved lower cuff arm 25 of FIG. 3. This may be advantageous in those instances wherein certain supination and pronation of the hand relative to the fixed position of the forearm prefer the use of a horizontal lower cuff arm 25B of FIG. 4 and not curved lower cuff arm 25 of FIG. 1. As was discussed relative to FIG. 3, vertical adjustment portion 17 securely clamps one end of lower cuff arm 25B and holds the lower cuff arm 25B in an immovable position. When it is desired to vertically adjust the height of the lower cuff arm 25B relative to the central axis 36, the knob 19 is turned so that the clamping action on the lower cuff arm 25B is reduced. Thereafter, the lower cuff arm 25B is raisable in the same manner as was discussed with regards to the illustration of FIG. 4.

Positioned on a top portion at an opposite (elbow-end) end of the lower cuff arm 25B is a center cuff 44 for resting the patient's elbow when using the present orthosis. The center cuff 44 is preferably fixed to the lower cuff arm 25B. In another embodiment, snap-on attachments of varying sizes, shapes, widths, etc., are attachable to the lower cuff arm 25B based on the medical practitioner's assessment of the patient's particular needs. Further, individual center cuffs would facilitate manufacture, shipping, and assembly of the orthosis thereby making the present orthosis more cost effective. In an embodiment that is not illustrated, the center cuff 44 slides along a track on the top of lower cuff arm 25B in a direction that is coincident to axis 36.

The center cuff 44 is engageable with a lower portion of a patient's arm, which is intended to rest directly on the center cuff. The center cuff 44 is not intended to restrain movement of bones in the lower portion of the arm during use of the orthosis. The center cuff 44 increases the comfort of the patient by providing a resting surface for the lower arm. In this embodiment, no straps are associated with the center cuff although alternative embodiments have a cuff configured to secure the arm to the lower cuff arm in a manner similar to how the lower cuff 32 secures the hand and wrist to plate 210 of the main gear assembly 48 (FIG. 1). The lower portion of the patient's arm is free to move relative to the upper portion of the arm when the patient's hand is being rotated by the main gear assembly about axis 36.

The center cuff 44 is preferably molded or otherwise formed of the polymeric material similar to that used to construct the other cuffs of the various orthosis embodiments provided herein. A preferred material is one which is cushioned (foam or synthetic fiber), non-allergenic, easily cleaned and/or sterilized (before or after use), and one which is easy to manufacture and environmentally friendly upon disposal.

As with the embodiment of FIG. 3, the embodiment of FIG. 4 also preferably enables the slideable attachment thereto at one end of one upper cuff arm assembly found in the art such as that disclosed in U.S. Pat. No. 5,848,979 to Bonutti et al. Such an upper cuff arm assembly would attach to the lower cuff arm 25B for gripping the patient's upper arm and holding it in a fixed position relative to the rotation of the hand. The attached upper cuff arm assembly is preferably telescopically adjustable along the center axis of the lower cuff arm and adjustable along an angle formed between the upper cuff arm and the lower cuff arm.

The various portions of the orthosis of the invention are preferably of unitary composite construction either collectively as a single piece or individually in parts. Construction processes are known in the art of manufacturing and comprise, for example, a molding, stamping, and the like. The materials with the present orthosis include, for example, a metallic, plastic, ceramic, composite, or other material offering adequate structural strength/weight trade-offs sufficient to enable the intended purposes of the present orthosis device as described herein. Other construction methods and materials are envisioned.

Although the lower cuff arm 25b of the embodiment of FIG. 4 does not show a slot at one end as shown at 164 in the lower cuff arm 25 of FIG. 3, an upper cuff arm could nevertheless be fitted thereon. The upper cuff arm slides over an opposite end of the lower cuff arm 25b and is secured in place by a set-screw. Such an upper cuff arm attachment would provide for gripping the patient's upper arm and holding it in a fixed position relative to the rotation of the hand. The upper cuff arm preferably being adjustable along lower cuff arm 25b and along an angle formed between the upper cuff arm and the lower cuff arm. The declination of the forearm relative to the upper arm is preferably adjustable and can be securely fixed at a desired angle by the medical practitioner to achieve the desired therapeutic effect.

Reference is now being made to the embodiment of the orthosis pictorially illustrated in FIG. 7 illustrating the embodiment of FIG. 3 showing a center cuff 44 and one embodiment of an upper cuff arm for securing the upper arm to the orthosis.

In the embodiment of the orthosis of FIG. 7, plate 43 is fixed to lower cuff arm 25 upon which the center cuff 44 is secured. The center cuff 44 is similar to the center cuff 44 discussed in detail in relation to FIG. 4. The center cuff 44 is securely fastened to plate 43 either by a rivet, hook and loop fastener, slip, or adhesive. Alternative means for attaching center cuff 44 to plate 43 are commonly found in the arts.

The embodiment of the orthosis of FIG. 7 also includes an upper cuff arm 26 illustrating one embodiment of a previously discussed upper cuff arm for securing the patient's upper arm to the orthosis. Generally, the upper arm cuff 26 is secured to the lower cuff arm 25 by a pin 31P passing therethrough. The pin 31P threadably engages knob 31 through the slot 164. The embodiment of the upper cuff arm 26 of FIG. 7 further generally includes a retractable member 41 that is held in place by a knob 27. The knob 27 is rotatable about an axis 27A in a direction circumferential to 27C. Further, the angle Θ formed between the lower cuff arm 25 and the upper cuff arm 26 can be adjusted. Although this angle Θ would ordinarily be set at 90°, some clinical situations would require another angle. For example, if the patient has limited or restricted flexion/extension, an angle other than 90° would be used.

Figure 8:
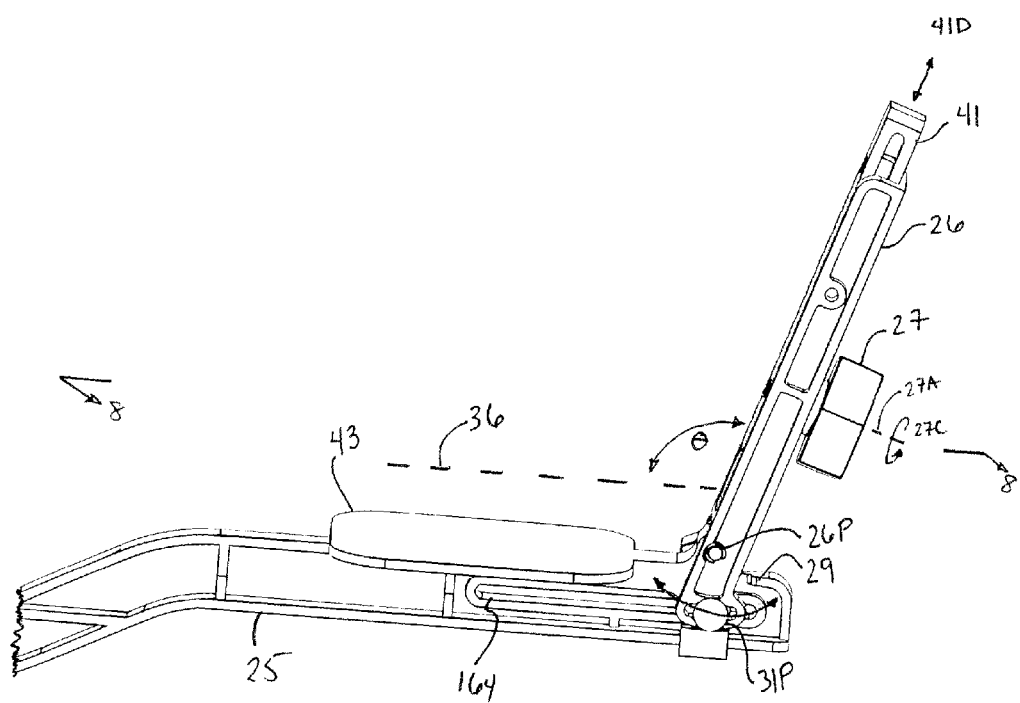
FIG. 8 is partial, right-side sectional view of the upper cuff arm shown in FIG. 7 taken along line 8-8 of FIG. 7.
Figure 9:
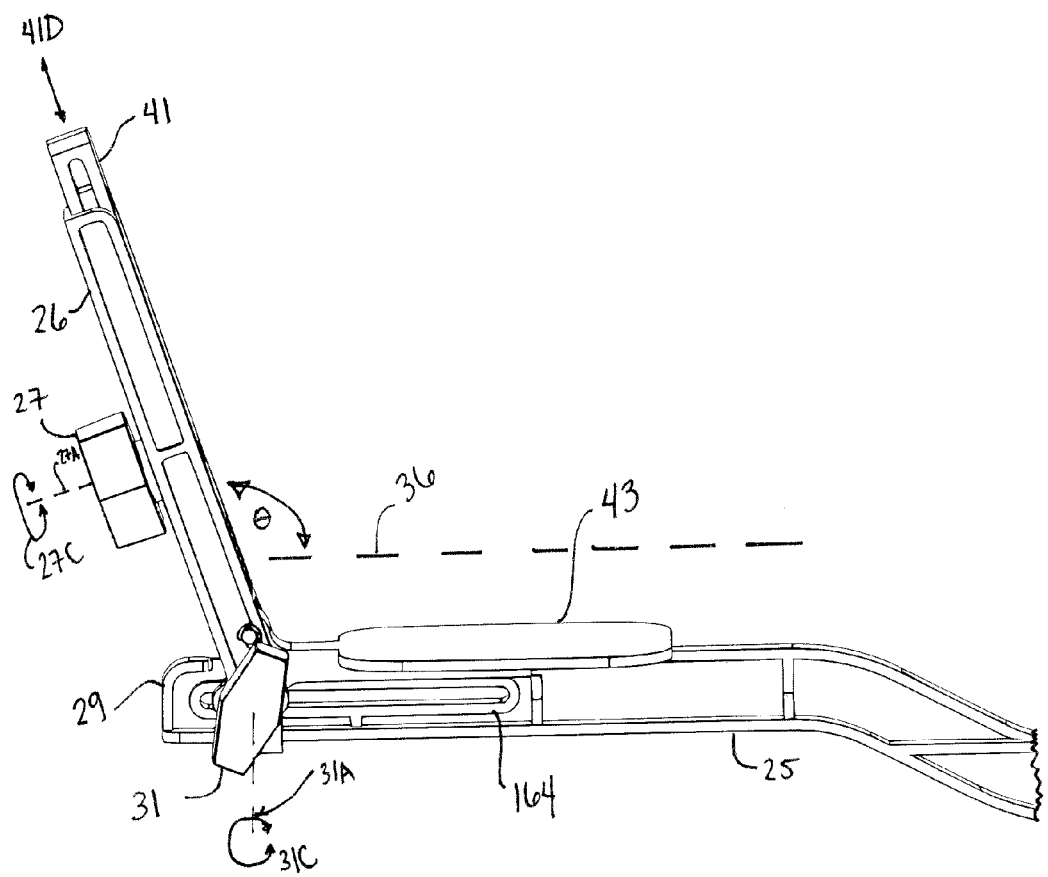
FIG. 9 is a left-side sectional view of the upper cuff arm shown in FIG. 7 taken along the line 9-9 of FIG. 7.
Figure 10:
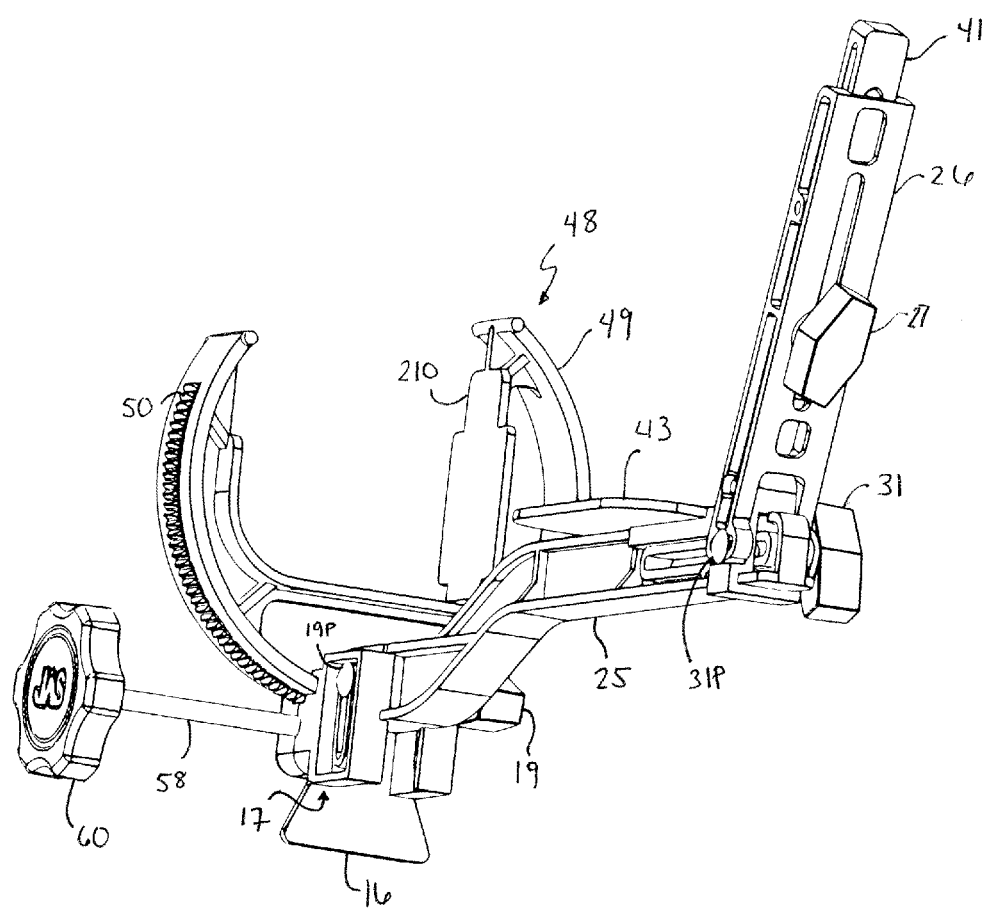
FIG. 10 is a bottom, left, rear oblique view of the embodiment shown in FIG. 7.

Reference is now additionally being made to FIGS. 8-10 which illustrate various perspectives of the embodiment of the upper cuff arm of FIG. 7.

The upper cuff arm 26 is physically attached to the lower cuff arm 25 by a pivot pin 26P. The pivot pin 26P is held in place by a c-clip common in the arts. The pin 26P passes through an outer portion of the upper cuff arm 26 and through a tab appendage on an upper portion of lower cuff arm 25, which has a hole therethrough The pin 26P provides a pivot connection between the upper cuff arm 26 and the lower cuff arm 25.

As shown in FIGS. 9 and 10, the knob 31 threadably engages the pin 31P. The pin 31P secures the upper arm cuff 26 to lower cuff arm 25 through the slot 164. The upper arm cuff 26 is slideably adjustable on the lower cuff arm 25 along an axis coincident with axis 36. When the knob 31 is tightened against the pin 31P by a rotation about axis 31A indicated by 31C, the position of the upper cuff arm 26 is held in a fixed position along the slot 164. When the knob 31 is loosened from its threaded engagement with the pin 31P by rotation about the axis 31A in a circumferential direction 31C, the upper cuff arm 26 is loosened from its fixed position along slot 164 and becomes slideably adjustable on the lower cuff arm 25.

Further, when the knob 31 is loosened from its threaded engagement with the pin 31P, the declination of upper cuff arm 26 can be changed relative to angle Θ (theta). When the upper cuff arm 26 is loosened, the upper cuff arm 26 can be pushed forward toward the main gear assembly 48 and the incident angle between the upper cuff arm and the lower cuff arm decreases. Such an action would have the effect of further bending the elbow thereby bringing the patient's forearm closer to the upper arm. Conversely, if the angle of incidence is increased by the upper cuff arm 26 being pushed away from the direction of the main gear assembly 48, then the patient's elbow would be extended and the forearm being straightened in relation to the patient's upper arm.

In certain instances, it may be desirable to completely unscrew the knob 31 and remove the pin 31P altogether from the orthosis apparatus while leaving the pivot pin 26P in place. This would be when the medical practitioner has determined that the patient's arm needs to be held virtually straight. When the knob 31 and the pin 31P are removed completely from the present orthosis, the upper cuff arm 26 declines backwards and pivots entirely on the pivot pin 26P. A full extension of the upper cuff arm 26 increases the angle (theta) to one hundred eighty degrees (180°). Hyper-extension of the elbow is prevented by a backstop 29. Alternatively, the backstop 29 is removable or the upper cuff arm is configured to not engage the backstop 29 when a slight hyper-extension of the elbow is deemed medically desirable. In such a manner, the angle of the patient's upper arm relative to the lower arm can be adjusted and held fixed by the present orthosis. This is preferable in those instances where the medical practitioner has determined that it is desirable to hold the patient's elbow at a certain angle during use.

Further illustrated in the embodiment of FIGS. 8 and 9 is a knob 27 that engages a slideable member 41 to hold the slideable member 41 in a fixed position. The slideable member 41 passes axially through a center of the upper cuff arm 26. When the knob 27 is rotated about an axis 27A in a direction circumferential to 27C, the slideable member 41 is released and made slideably extendable. In such a manner, the member 41 is adjustable outward or, alternatively, slideably retracted inward in either direction indicated by 41D. This may be important to the medical practitioner when it is deemed medically desirable to provide additional support to the patient's upper arm in addition to the support already provided by the upper cuff arm 26.

As shown in FIG. 11, which is a side elevation view of the embodiment of the orthosis of FIG. 7, the lower cuff 32 is secured to the main gear assembly 48 by secured attachment to the cuff support plate 210. The lower cuff 32 includes straps 122 and 130. The strap 122 for securing the patient's wrist inside the lower cuff is fixed to sidewall 110 of the lower cuff 32 by a rivet 122A. The strap 130 for securing the patient's hand inside the lower cuff 32 is fixed to the sidewall 110 of the lower cuff 32 by the rivet 130A. In addition, the center cuff 44 is secured to the plate 43 on the lower cuff arm 25. Fixed to a forward side of the upper cuff arm 26 is the upper cuff 42. The upper cuff 42 includes a pair of straps 144 and 146. The upper arm of the patient is gripped by the straps 144 and 146. The straps 144 and 146 pass through the rings 148 and 150, respectively, and are tightened. The discussion involving construction, materials, and alternatives thereto regarding the lower cuff 32 applies to the center cuff 44 and the upper cuff 42.

Attention is now respectfully directed to FIG. 12 showing the patient's arm positioned in the orthosis of FIG. 11. In this illustration, the patient's forearm 76 is resting on the center cuff 44 on the lower cuff arm 25. The patient's upper arm 66 is secured to the upper cuff arm 26 by the upper cuff 42. The upper arm 66 is strapped into the upper cuff 42 by straps 144 and 146. The straps 144 and 146 have been passed through rings 148 and 150, respectively, and tightened. In such a manner, the patient's upper arm 66 is held securely fastened to the upper arm 26 of the present orthosis apparatus. In addition, the patient's wrist 74 and hand 68 are secured in main gear assembly 48 by the lower cuff 32. The sidewall 110 of the lower cuff 32 has been pulled tight around the patient's wrist 74 and hand 68 by the two straps 122 and 130. The wrist portion being secured by the strap 122 and the hand portion being secured by the strap 130. Straps 122 and 130 are passed through the rings 126 and 132 (FIGS. 14 and 15) and tightened. As previously discussed, turning the knob 60 causes the rotation of the shaft 58. In turn, the shaft 58 rotates the worm gear 56 (FIG. 2) of the gear assembly 34. The worm gear 56, in turn, meshingly engages the gear teeth 49 of the arcuate member 50 (FIG. 2). In such a manner, the patient's wrist 74 can be rotated about the axis 36 (FIG. 1).

Viscoelastic body tissue connecting the proximal end portions 92 and 96 (FIG. 17) of the radius and ulna 84 and 86 with the humerus 100 in the arm 66 of a patient may require stretching to enable the hand 68 of the patient to move through a desired range of motion in supination and/or pronation. When the viscoelastic body tissue connected with the proximal end portions 92 and 96 of the radius and ulna 84 and 86 is to be stretched, the upper portion 80 of the arm 66 of the patient is positioned in the upper cuff 42 of the orthosis. The straps 144 and 146 (FIG. 12) are loosely tightened around the upper portion 80 of the arm to initially position the upper cuff arm relative to the upper portion 80 of the patient's arm. The lower cuff arm 25 is positioned relative to the lower portion 76 of the patient's arm. The upper cuff straps 144 and 146 and are tightened to firmly grip the upper portion 80 of the patient's arm, as shown in FIG. 13. In addition, the hand 68 is firmly gripped between the sidewall 110 of the lower cuff.

Until the main drive assembly 34 is actuated by the manual turning of knob 60 (FIG. 1), the lower portion 76 and the upper portion 80 of the patient's arm 66 are held against movement relative to each other. Thus, the lower portion 76 of the arm is held against movement relative to the lower cuff arm 24 by the lower cuff 32. The upper portion 80 of the arm 66 is held against movement relative to the upper cuff arm 26 by the upper cuff 42. At this time, the only way to move the arm 66 is at the shoulder 70.

Attention is respectfully directed to FIGS. 13 and 14. To supinate the hand (palm upward orientation), the knob 60 is rotated in a clockwise direction. This results in the drive gear 56 (FIG. 2) rotating the arcuate member 50 in a counterclockwise direction (viewed from the end closest to lower cuff 32). As the lower cuff 32 is rotated in a counterclockwise direction, the extent of supination of the hand 68 is increased as the hand is moved from the position shown in FIG. 13 toward the position shown in FIG. 14.

As the hand 68 is rotated from the position shown in FIG. 13 toward the position shown in FIG. 14, the sidewall 110 of the lower cuff 32 firmly grip the distal end portions 90 and 94 of the radius and ulna bones 84 and 86. This results in the radius and ulna bones being moved relative to the humerus 100 at the elbow 78. The direction of rotation of the knob 60 can then be reversed to move the hand 68 back toward the initial position of FIG. 13.

Attention is respectfully directed to FIGS. 13 and 15. To pronate the hand 68 from the initial orientation of FIG. 13 to the orientation of FIG. 15 (a palm downward orientation), the knob 60 is rotated in a counterclockwise direction. Counterclockwise rotation of the knob 60 causes the drive gear 56

(FIG. 2) to rotate arcuate member 50 about the axis 36 from the initial position shown in FIG. 13 toward the position shown in FIG. 15. As this occurs, the lower cuff 32 firmly grips the distal end portions of the radius and ulna. The distal end portions of the radius and ulna begin to rotate with the lower cuff 32 about the axis 36.

As the lower cuff 32 continues to rotate, the proximal end portions of the radius and ulna move relative to the distal end portion 102 of the humerus. The radius 84 will revolve partially about the ulna 86. The proximal end portion 96 of the ulna will articulate with the distal end portion 102 of the humerus 100. The rotational motion imparted by the lower cuff 32 to the distal end portions of the radius and ulna will be isolated to the region between the elbow 78 and wrist 74 in the arm of the patient.

As the drive gear 56 continues to rotate, the main gear 48 and the lower cuff 32 are rotated together in a clockwise direction (viewed from the end) about the axis 36. As this occurs, the extent of pronation of the hand 68 is increased. Rotation of the drive gear 56 may be interrupted after the lower cuff 32 has moved partway from the initial position shown in FIG. 13 toward the palm downward orientation shown in FIG. 15. Upon interruption of the rotation of drive gear 56, the drive gear is effective to hold arcuate member 50 against further rotation.

This results in stretched viscoelastic material connected with the proximal end portions of the radius and ulna being held in a stretched condition. After a short time, the viscoelastic material begins to relax. The knob 60 can then be further rotated in a counterclockwise direction to further stretch the viscoelastic material interconnecting the proximal end portions of the radius and ulna and the humerus.

Reversing the direction of rotation of the knob 60 rotates the drive gear 56 and the arcuate member 50 to move the lower cuff 32 in a reverse direction. Continuous rotation of knob 60 in a clockwise direction causes the lower cuff 32 and main gear 48 to be rotated from the positions shown in FIG. 15 back to the initial positions shown in FIG. 13. As this occurs, the extent of pronation of the hand 68 is decreased.

The present invention can further include a monitor for use with the orthosis, which provides assurances the patient is properly using the orthosis during his/her exercise period. For instance, the monitor can have a position sensor, a temperature sensor, a force sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly.

This analysis may be conducted remotely, thereby saving the time and expense of a home visit by a healthcare professional or technician. An exemplary monitoring system is provided in U.S. Publication No. 20040215111 entitled "Patient Monitoring Apparatus and Method for Orthosis and Other Devices," to Bonutti et al., the content of which is herein expressly incorporated by reference in its entirety.

The components of the present invention are rigid members made of, for example, aluminum, stainless steel, polymeric, or composite materials. The member and extensions are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

In a method of manufacture, the cuffs can include a base plate having a plurality a strap attached thereto, where the straps are position about a body portion of a patient. The straps are attached to the base plate using fastener elements, such as screws threaded into the base plate. The screws can be removable to allow for easy removal and/or replacement of the straps.

Alternatively, in an embodiment where the base plate is made of a polymeric material, the straps can be welded to the base plate using an energy welding technique such as, RF welding, ultrasonic welding, high frequency welding, etc. For example, in ultra-sonic welding an acoustic tool in used to transfer vibrational energy into the weld areas of the straps and the base plate. The friction of the vibrating molecules generates heat, which melts the surface material of the base plate in the welding area, at which point the vibrational energy is stopped. Pressure is applied to the strap and the base plate, allowing the melted material to solidify within the material of the strap. In this method the strap is secured to the base plate without the need of fasteners.

Similarly, where the cuffs are made of a polymeric material, the cuff can be welded to the orthosis using energy welding techniques. For example, the cuffs can be made of a substantially rigid, flexible, or fabric polymeric material which can be welded directly onto the arm members of the orthosis. It is also contemplated that the straps can be an integral part of the cuffs. For example, where the cuffs are made of a polymeric fabric, the straps can be integrally formed in the fabric pattern when making the cuffs.

Although it is preferred to use the orthosis to effect supination and/or pronation of the hand 68, it is contemplated that the orthosis could be modified to be used with other portions of a patient's body if desired. For example, the orthosis 10 could be constructed in such a manner as to effect pronation and/or supination of a foot of a patient.

Figure 18:
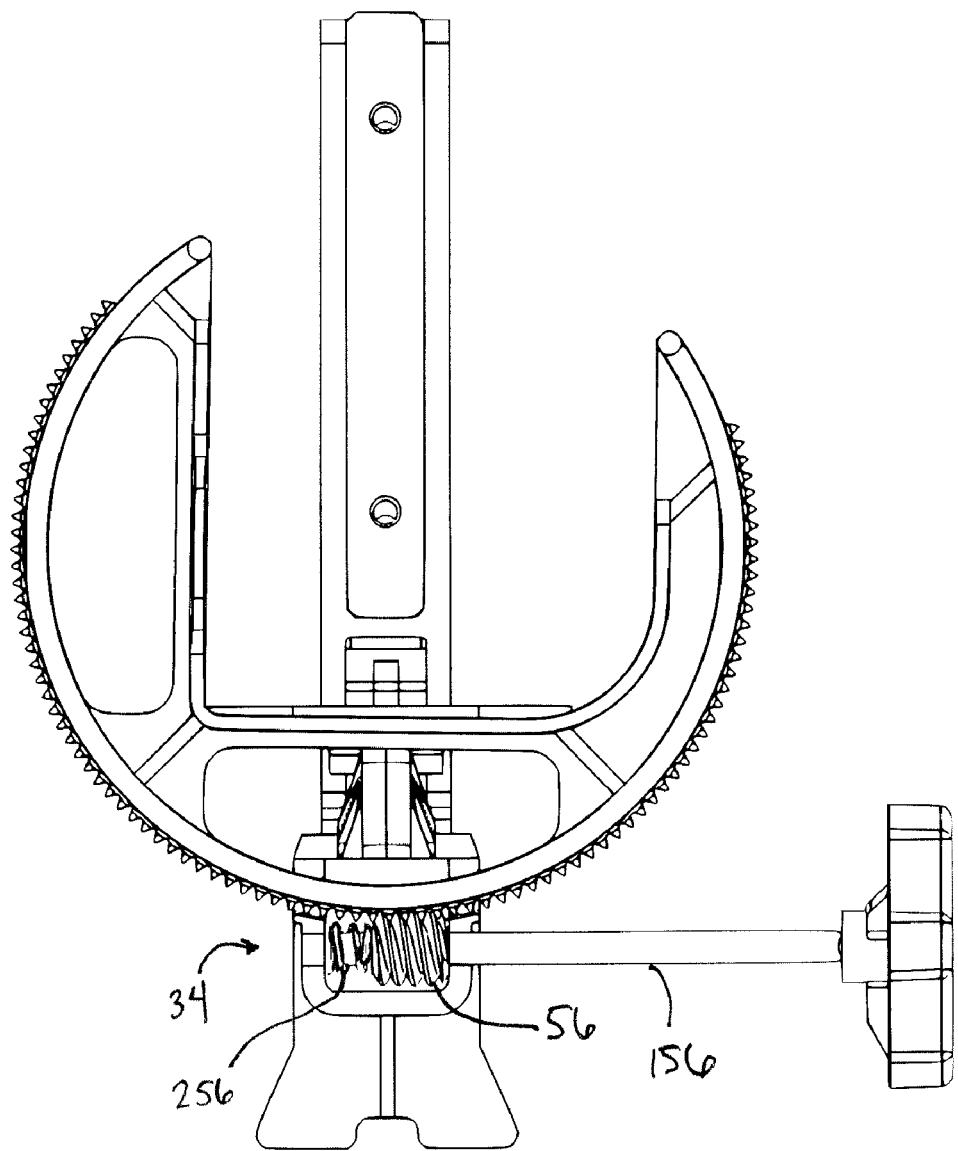
FIG. 18 is a front side view of an embodiment of the orthosis apparatus having a spring on an axle.

FIG. 18 shows an embodiment of the orthosis device having a spring 256 disposed on an axle 156 of the drive gear 56. The spring 256 is coaxial with the axle 156. The spring 256 is helical and wrapped around the drive gear 56. In the embodiment shown, the spring 256 is sandwiched between the drive gear 56 and a wall of the drive assembly 34. The spring 256 resists both compressive and tensile loads. A second spring (which is not illustrated) may be included on the other side of the drive gear 56 and a second wall that opposes the wall abutting the first spring. The spring 256 provides tension on the drive gear 56 and prevents the arcuate member 50 from rotating unintentionally. Likewise, the spring 256 provides tension to prevent the muscles being stretched from moving to a neutral position when being stretched.

In view of the foregoing description, it is apparent that the present invention provides a new and improved apparatus and method for use in effecting relative movement between bones in an arm 66 or other portion of a body of a patient.

In summary, what is disclosed is a new and improved method and apparatus for use in effecting relative movement between a patient's hand and the bones in the patient's arm. The novel apparatus includes a main gear assembly having a lower cuff affixed there through for gripping a wrist and hand. The lower cuff centers the longitudinal axis of the forearm during rotational distal adjustment. The main drive assembly rotatably varies the extent of pronation and/or supination of the hand of the patient. A lower cuff arm connects, on one end, a vertical adjustment portion integral to the main gear assembly. The longitudinal axis of the patient's forearm coincident with the longitudinal axis of the lower cuff arm. The lower cuff arm has a center cuff affixed thereon upon which the patient's arm rests during the use of the present apparatus. The lower cuff arm being vertically adjustable relative to the fixed position of the rotatable drive assembly gripping the patient's hand. An upper cuff arm slideably attaches to an opposite end of the lower cuff arm at a point located behind the center cuff for gripping the patient's upper arm and holding it in a fixed position relative to the rotation of the hand. The slideable upper cuff arm being adjustable both along the center axis of the lower cuff arm and along an angle formed between the patient's upper arm and the lower cuff arm. The declination of the forearm relative to the upper arm is adjustable and can be securely fixed at a desired angle by the medical practitioner to achieve the desired therapeutic effect. The interchangeability of the different parts of the orthosis of the present invention effectuates the device's assembly/disassembly and the interchangeability of parts to meet the patient's therapeutic needs.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

All references cited herein are expressly incorporated by reference in their entirety.

What is claimed is:

1. An orthosis apparatus for rotating a medial bone of an appendage relative to a proximal bone of the appendage about a longitudinal axis of the distal bone, the appendage having a distal bone connected to the medial bone, said apparatus comprising:
    an arcuate member being rotatable about a central axis;
    an array of gear teeth disposed about said arcuate member;
    a lower cuff connected to said arcuate member and being configured to secure the distal bone and to align the medial bone along said central axis; and
    a drive gear mechanically communicating with said gear teeth such that rotating said drive gear causes said arcuate member to rotate circumferentially about said central axis thereby pronating and supinating the medial bone.

2. The orthosis apparatus according to claim 1, further comprising an upper cuff arm being connected to said lower cuff and being configured to secure the proximal bone.

3. The orthosis apparatus according to claim 2, further comprising a lower cuff arm interconnecting said arcuate member and said upper cuff arm.

4. The orthosis apparatus according to claim 3, further comprising a center cuff connected to said lower cuff arm configured to support the medial bone.

5. The orthosis apparatus according to claim 4, wherein said central cuff retards rotation of the medial bone when rotating the distal bone with said arcuate member.

6. The orthosis apparatus according to claim 3, further comprising a pivot interconnecting said lower cuff arm and said upper cuff arm, said pivot being configured to allow the proximate bone to articulate relative to the medial bone.

7. The orthosis apparatus according to claim 3, wherein said upper cuff arm includes a retractable slideable member, said slideable member extending and retracting longitudinally along said upper cuff arm, said slideable member being configured to support the proximate bone.

8. The orthosis apparatus according to claim 3, wherein:
    said lower cuff arm has a slot formed therein, said slot running at least partially axially; and
    a pin connected to said upper cuff arm is disposed in said slot to allow said upper cuff arm to adjust for different sizes of the medial bone.

9. The orthosis apparatus according to claim 8, further comprising a means for releasably fixing a position of said lower cuff relative to said upper cuff.

10. The orthosis apparatus according to claim 1, further comprising a lower cuff arm being connected to said arcuate member and being movable relative to said central axis.

11. The orthosis according to claim 10, further comprising a drive assembly housing said drive gear and at least a portion of said arcuate member;
    one of said drive assembly and said lower cuff arm having a slot formed therein, said slot travelling relative to said central axis; and
    one of said drive assembly and said lower cuff, not having said slot, having a pin connected thereto and travelling in said slot.

12. The orthosis apparatus according to claim 11, further comprising a means for releasably fixing a position of said lower cuff arm relative to said drive assembly.

13. The orthosis device according to claim 1, further comprising a means for aligning a longitudinal axis of the medial bone with said central axis.

14. The orthosis apparatus according to claim 1, further comprising a protective plate disposed beneath said arcuate member.

15. The orthosis apparatus according to claim 1, wherein said drive gear is a worm gear.

16. The orthosis apparatus according to claim 1, further comprising:
    a shaft connected to and turning said drive gear; and
    a knob connected to said shaft for rotating said shaft.

17. The orthosis apparatus according to claim 1, further comprising a drive assembly retaining said drive gear against movement in a direction transverse to said central axis whenever said arcuate member is rotated.

18. The orthosis apparatus according to claim 16, further comprising a protective plate disposed beneath said arcuate member, said protective plate being tall enough to provide clearance for said knob.

19. The orthosis according to claim 1, wherein said arcuate member has a U-shaped cuff support disposed therein, said U-shaped cuff support supporting said lower cuff.

20. The orthosis apparatus as in claim 1, wherein said lower cuff includes:

a first section overlying a first side of the distal bone;
a second section overlying a second side of the distal bone; and
a means for urging said first section and second section toward each other to secure the distal bone.

21. The orthosis apparatus according to claim 1, further comprising a center cuff connected to lower cuff arm and being configured to support the medial bone.

22. The orthosis apparatus according to claim 1, wherein said lower cuff arm is axially movable relative to said arcuate member.

23. The orthosis apparatus according to claim 1, wherein said lower cuff arm is aligned parallel to said central axis so both lie in a plane, and said lower cuff arm being movable relative to said arcuate member in said plane.

24. The orthosis apparatus according to claim 1, wherein said lower cuff arm is movable relative to said arcuate member.

25. The orthosis apparatus according to claim 1, further comprising an upper cuff arm pivotally connected to said lower cuff arm.

26. The orthosis apparatus according to claim 1, further comprising an upper cuff arm connected to said lower cuff arm, said upper cuff arm being axially slideable along said lower cuff arm.

27. The orthosis apparatus according to claim 1, wherein said lower cuff includes a palmer plate.

28. The orthosis apparatus according to claim 27, wherein said palmer plate includes a bump for complementing a palm of a patient.

29. The orthosis apparatus according to claim 1, wherein said lower cuff is further configured to secure to the medial bone.

30. An orthosis apparatus for rotating a bone about a bone axis, comprising:
an arcuate member configured to at least partially surround the forearm axis, said arcuate member being configured to be connected to the forearm;
a means for rotating said arcuate member about an arcuate member axis, said arcuate member axis being circumscribed by said arcuate member; and
a means for aligning said arcuate member axis with the forearm axis.

31. The orthosis apparatus according to claim 30, further comprising:
a means for isolating the forearm axis in a given plane; and
a means for maintaining said arcuate member axis in said given plane when said means for aligning said arcuate member is operated.

32. The orthosis apparatus according to claim 31, wherein said means for maintaining said arcuate member axis in said given plane includes a track disposed in one of in said plane and parallel to said plane, said arcuate member traveling along said track.

33. The orthosis apparatus according to claim 30, wherein said arcuate member defines a plane, said plane being orthogonal to the forearm axis.

34. The orthosis apparatus according to claim 30, further comprising a means for coplanar aligning said arcuate member axis and the forearm axis.

35. The orthosis apparatus according to claim 34, wherein said means for coplanar aligning said arcuate member axis and the forearm axis includes a beam fixed parallel to the forearm axis and a track disposed perpendicular to said beam and the forearm axis and connected to said beam, said arcuate member being traveling on said track, and said arcuate member axis being aligned parallel to said beam.

36. The orthosis apparatus according to claim 30, wherein said means for rotating said arcuate member includes an array of gear teeth disposed on a periphery of said arcuate member and a drive gear communicating with said gear teeth, said drive gear rotating said arcuate member about said arcuate member axis by rotating said drive gear.

37. The orthosis apparatus according to claim 30, wherein said means for aligning said arcuate member axis with the forearm axis includes a track not parallel to the forearm axis, said arcuate member traveling on said track to move said arcuate member in relation to the forearm axis.

38. The orthosis apparatus according to claim 30, wherein said means for isolating the forearm axis in a given plane includes a beam running parallel to the forearm axis and connected to the forearm.

39. An orthosis apparatus for rotating a forearm about a forearm axis, the forearm being connected to a wrist an elbow, the orthosis apparatus comprising:
an arcuate member rotatable about an arcuate member axis substantially coincident to a forearm axis defined by a line extending along the forearm from the wrist to the elbow;
an array of gear teeth disposed about said arcuate member;
a drive gear mechanically communicating with said gear teeth and configured to rotate said arcuate member about said arcuate member axis whenever said drive gear is rotated;
a knob operably connected to said drive gear; and
a protective plate connected to said arcuate member and providing clearance for said knob to be rotated.

40. An orthosis apparatus for rotating a forearm about a forearm axis, comprising
an arcuate member rotatable about an arcuate member axis;
an array of gear teeth disposed about said arcuate member;
a drive gear mechanically communicating with said gear teeth and configured to rotate said arcuate member about said arcuate member axis whenever said drive gear is rotated, said drive gear having an axle; and
a spring disposed on said axle of said drive gear to provide tension against said drive gear rotating in at least one direction.

41. The orthosis apparatus according to claim 40, wherein said spring is coaxial with said axle.

42. The orthosis apparatus according to claim 41, wherein said spring is helical and disposed about said axle.

43. In an orthosis apparatus for rotating a forearm about a forearm axis including an arcuate member rotatable about an arcuate member axis, an array of gear teeth disposed about said arcuate member, a drive gear mechanically communicating with said gear teeth and configured to rotate said arcuate member about said arcuate member axis whenever said drive gear is rotated, said drive gear having an axle, the improvement comprising:
a spring disposed on said axle of said drive gear to provide tension against rotating of said drive gear.

44. A method for performing an orthosis on an appendage having a distal bone, a medial bone, and a proximal bone, which comprises:
providing an arcuate member having a central arcuate member axis;
securing the proximal bone with an upper cuff;
aligning said arcuate member axis with a medial-bone axis by moving said arcuate member in relation to said upper cuff;
fixing a hand of the patient to said arcuate member; and rotating said arcuate member about said arcuate member axis.

45. The method according to claim 44, which further comprises:
- isolating the medial bone and the proximal bone in a given plane during the fixing step; and
- moving said arcuate member in said given plane during the aligning step.

46. A method of preventing an orthosis apparatus from unintentionally rotating, which comprises:
- providing an orthosis apparatus for rotating a forearm about a forearm axis, the orthosis including an arcuate member rotatable about an arcuate member axis; and
- retarding a rotation of said orthosis apparatus in at least one direction an array of gear teeth disposed about said arcuate member and a drive gear mechanically communicating with said gear teeth and configured to rotate said arcuate member about said arcuate member axis whenever, said drive gear is rotated, said drive gear having an axle.

47. The method according to claim 46, which further comprises:
- rotating said orthosis apparatus with a drive gear having an axle of rotation; and
- disposing a spring about said axle of said drive gear to provide tension against said drive gear rotating in at least one direction.

48. The method according to claim 46, wherein said orthosis device includes:
- a spring disposed on said axle of said drive gear to provide tension against said drive gear rotating in at least one direction.

\* \* \* \* \*